(12) United States Patent
Gupta

(10) Patent No.: US 9,546,940 B2
(45) Date of Patent: Jan. 17, 2017

(54) TEST DEVICE FOR DETERMINING THREE-DIMENSIONAL CONSOLIDATION PROPERTIES OF SOILS

(71) Applicant: Ramesh Chandra Gupta, Ashburn, VA (US)

(72) Inventor: Ramesh Chandra Gupta, Ashburn, VA (US)

(*) Notice: Subject to any disclaimer, the term of this patent is extended or adjusted under 35 U.S.C. 154(b) by 0 days.

(21) Appl. No.: 15/170,661

(22) Filed: Jun. 1, 2016

(65) Prior Publication Data

US 2016/0356685 A1 Dec. 8, 2016

Related U.S. Application Data

(63) Continuation-in-part of application No. 14/729,157, filed on Jun. 3, 2015.

(51) Int. Cl.
*E02D 1/02* (2006.01)
*G01N 3/08* (2006.01)
*G01N 33/24* (2006.01)

(52) U.S. Cl.
CPC .............. *G01N 3/08* (2013.01); *G01N 33/24* (2013.01); *E02D 1/025* (2013.01); *E02D 1/027* (2013.01)

(58) Field of Classification Search
CPC ........ E21B 49/006; E02D 1/022; E02D 1/025; E02D 1/027; G01N 3/08; G01N 3/00; G01N 3/10; G01N 33/24
USPC ......... 73/784, 785, 788, 789, 790, 798, 803, 73/760
See application file for complete search history.

(56) References Cited

U.S. PATENT DOCUMENTS

| | | | | |
|---|---|---|---|---|
| 4,122,704 A | * | 10/1978 | Lutenegger | G01N 3/10 73/822 |
| 4,542,655 A | * | 9/1985 | Park | G01B 5/30 73/152.59 |
| 5,025,668 A | * | 6/1991 | Sarda | G01N 3/10 73/795 |
| 5,226,310 A | * | 7/1993 | Steiger | E21B 49/006 73/38 |

(Continued)

FOREIGN PATENT DOCUMENTS

| | | | | |
|---|---|---|---|---|
| JP | 52030488 A | * | 3/1977 | |
| SU | 1425516 | * | 9/1988 | |

OTHER PUBLICATIONS

Translation of Yamano (JP 52030488) Abstract.*

(Continued)

*Primary Examiner* — Lisa Caputo
*Assistant Examiner* — Nathaniel T Woodward

(57) ABSTRACT

A test device has been invented for determining three-dimensional consolidation properties of soils, using a flexible ring permitting displacements and dissipation of the excess pore pressures in both horizontal and vertical directions, and affording determination of coefficients of consolidation in the horizontal and vertical directions, and the modulus of elasticity. The flexible ring consists of a filter fabric around the soil specimen, a rubber membrane around the filter, circular shaped segmented metal plates around the membrane and rubber bands or rings around the plates. Both the incremental loading or triaxial type loading systems can be used with this device. A calibration device for calibration of the flexible ring is used to determine the modulus of elasticity of elastic elements, required for calculating lateral resistance provided by the flexible ring during the test.

4 Claims, 17 Drawing Sheets

(56) References Cited

U.S. PATENT DOCUMENTS

| | | | | |
|---|---|---|---|---|
| 5,275,063 | A | * | 1/1994 | Steiger ............... G01N 33/241 73/865.6 |
| 5,435,187 | A | * | 7/1995 | Ewy ....................... G01N 3/10 73/38 |
| 6,595,068 | B2 | * | 7/2003 | Brovold ................. G01N 3/10 73/803 |
| 6,655,220 | B1 | * | 12/2003 | Reiffsteck ............... E02D 1/04 73/152.59 |
| 7,520,177 | B2 | * | 4/2009 | Secq ....................... G01B 5/30 73/795 |
| 7,536,921 | B1 | * | 5/2009 | Chu ........................ G01N 3/10 73/760 |
| 7,694,581 | B2 | * | 4/2010 | Secq ....................... G01B 5/30 73/760 |
| 2005/0039540 | A1 | * | 2/2005 | Crockford ............ G01L 5/0004 73/784 |
| 2010/0089124 | A1 | * | 4/2010 | Katti ..................... E02D 1/027 73/38 |

OTHER PUBLICATIONS

Translation of Bargatin (SU 1425516) Abstract.*

ASTM Standards, Standard Test Method for Determining One-Dimensional Consolidation Properties of Soils,2011,ASTM D2435/D2435 M-11,American Society of Materials,Philadelphia,US.

ASTM Standards, Standard Test Method for Consolidated Undrained Triaxial Compression Test for Cohesive Soils,2011,ASTM: D4767-1,American Society of Materials, Philadelphia,US.

AASHTO, Standard Method of Test for One-Dimensional Consolidation Properties of Soils, 2012, American Association of State Highway and Transportation Officials, Washington,US.

Fang, H, Foundation Engineering Handbook, 1990, 2nd Edition, Van Nostrand Reinhold, New York.

HRB, Estimating Consolidation Settlements of Shallow Foundations on Overconsolidated Clay,1973, Application Bulletin by Committee A2L02, Properties of Soli and Rock.

Perloff, W. H., and Baron, W. (1976), Soil Mechanics, John Wiley and Sons, New York.

Skempton, A. W., and Bjerrum, L. (1957), A Contribution to the Settlement Analyses of Foundations on Clay, Geotechnique 7, No. 3.

Terzaghy, K, Peck, B. P., Mesri, G. (1996), Soil Mechanics in Engineering Practice, Wiley-Interscience, New York.

Winterkorn H. F., and Fang, H. (1975), Foundation Engineering Handbook, Van Nostrand Reinhold Company, New York.

* cited by examiner

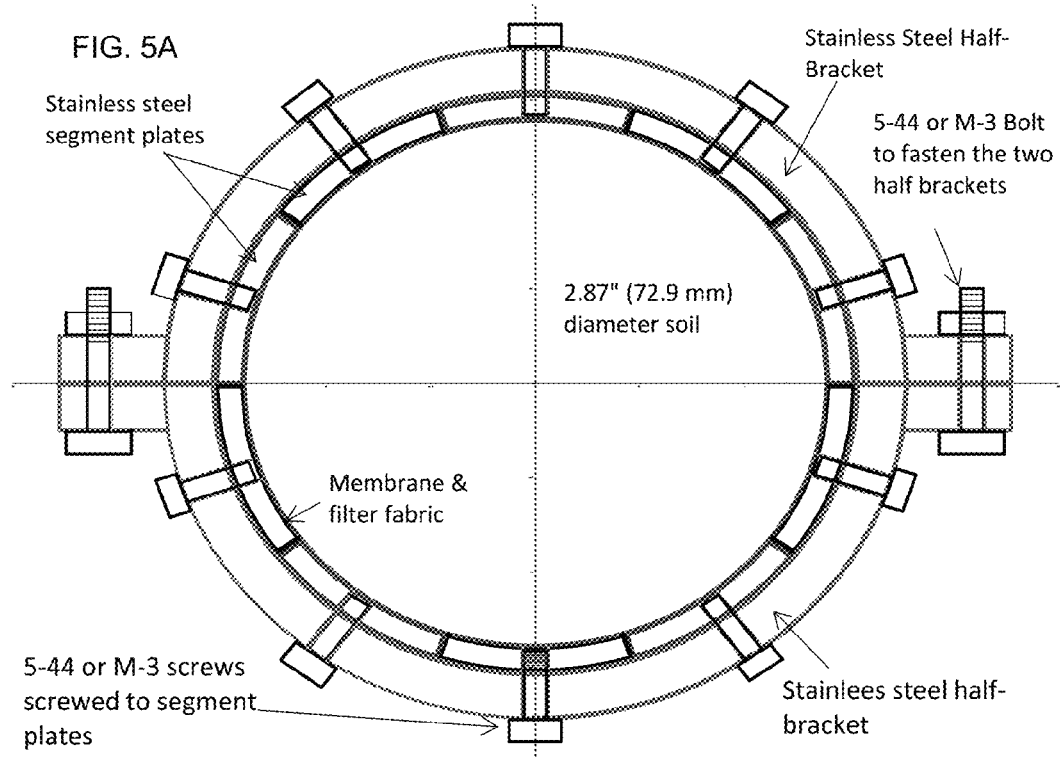
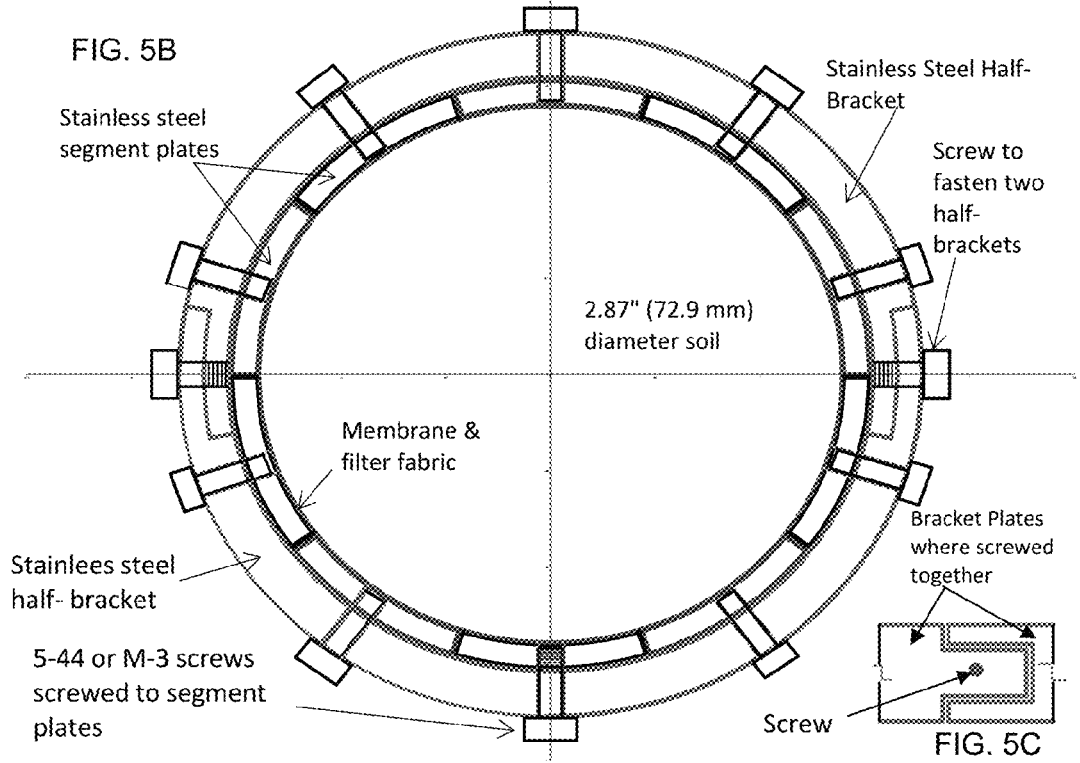

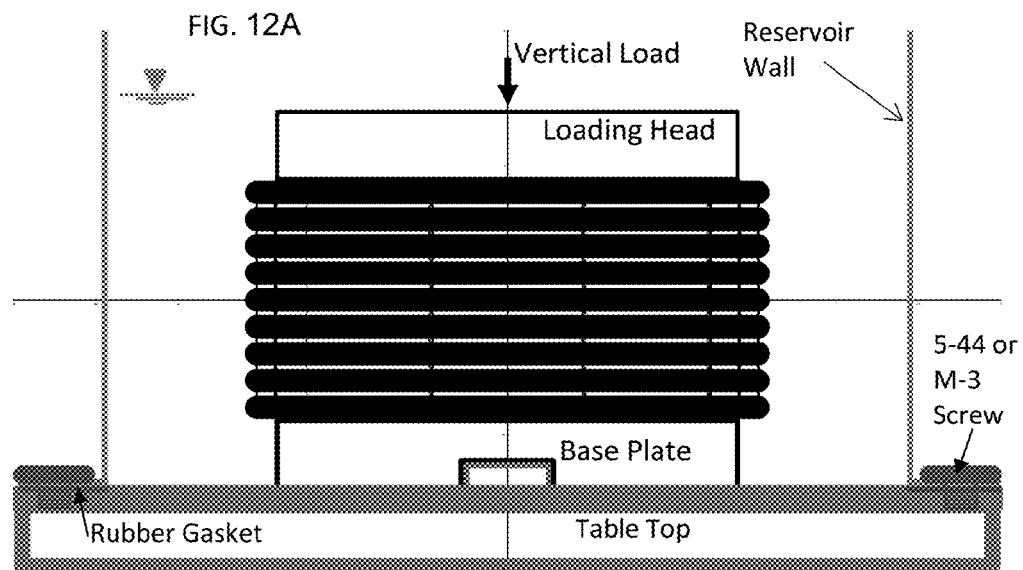
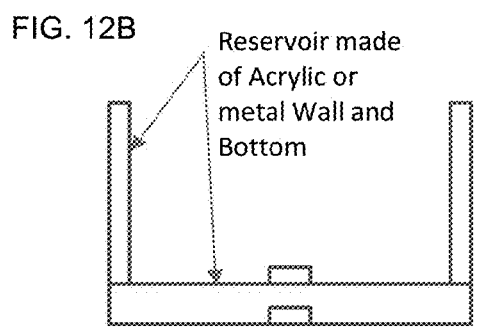
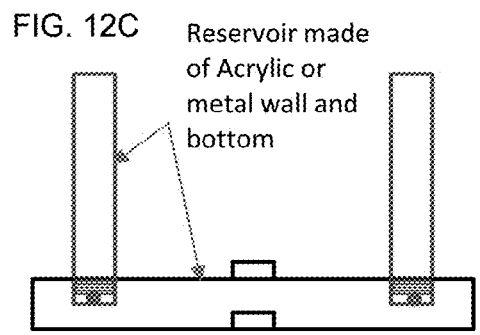
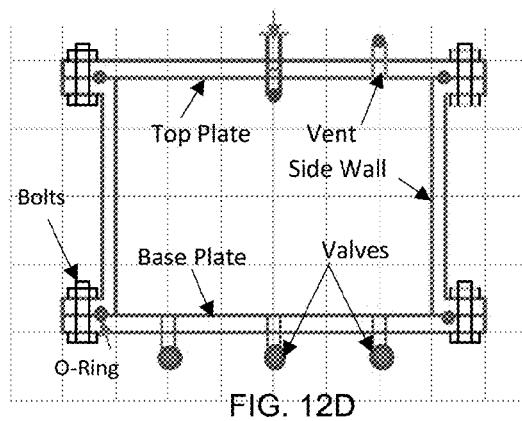
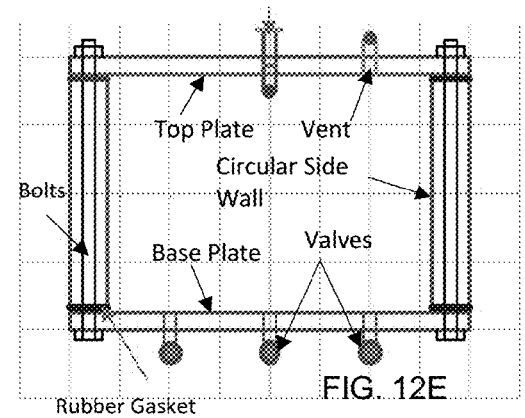

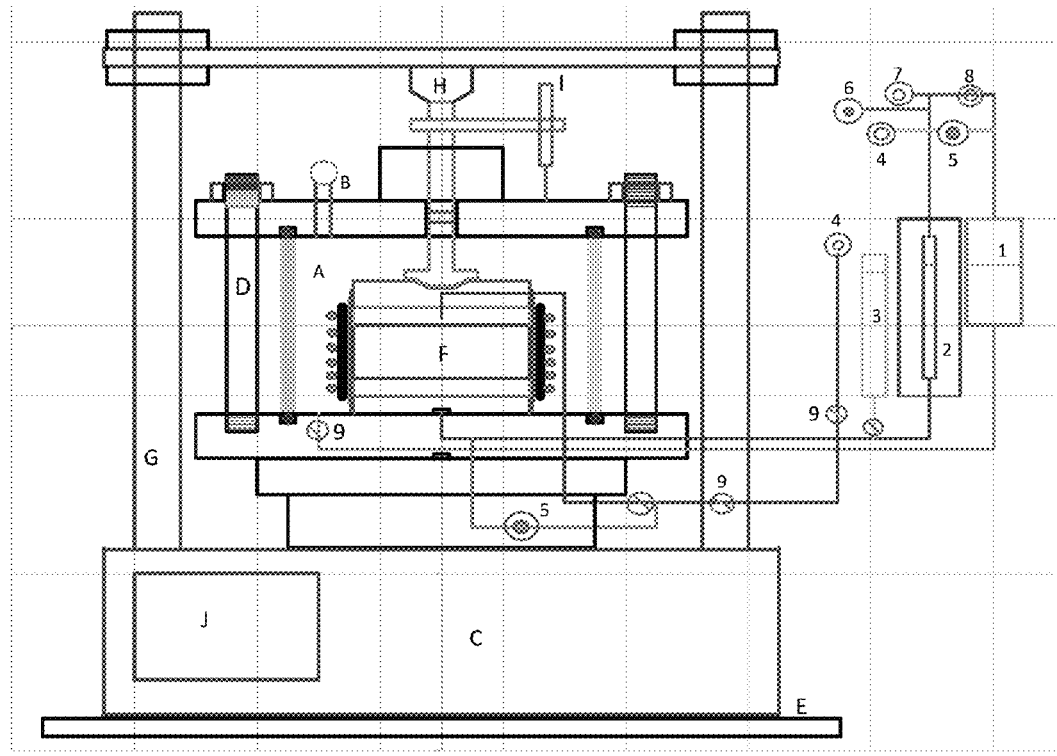

LEGEND

For Control Panel
1 Chamber Pressure Reservoir
2 Volume Change Burette
3 Water Reservoir
4 Vacuum Regulator
5 Differential Pressure Transducer
6 Back Pressure Transducer
7 Back Pressure Regulator
8 Cell Pressure Regulator (Differential)
9 Valves

For Chamber and Loading Device
A Acrylic Chamber/Cell
B Vent
C Axial Loading Device
D Clamping Rods for Chamber
E Table Top
F 3-D Consolidation Test Sample Assembly
G Loading Frame with Rods
H Load Cell (or Prooving Ring)
I Deformation Transducer (or Dial Gage)
J Regulator Board for Strain Rates

FIG. 15

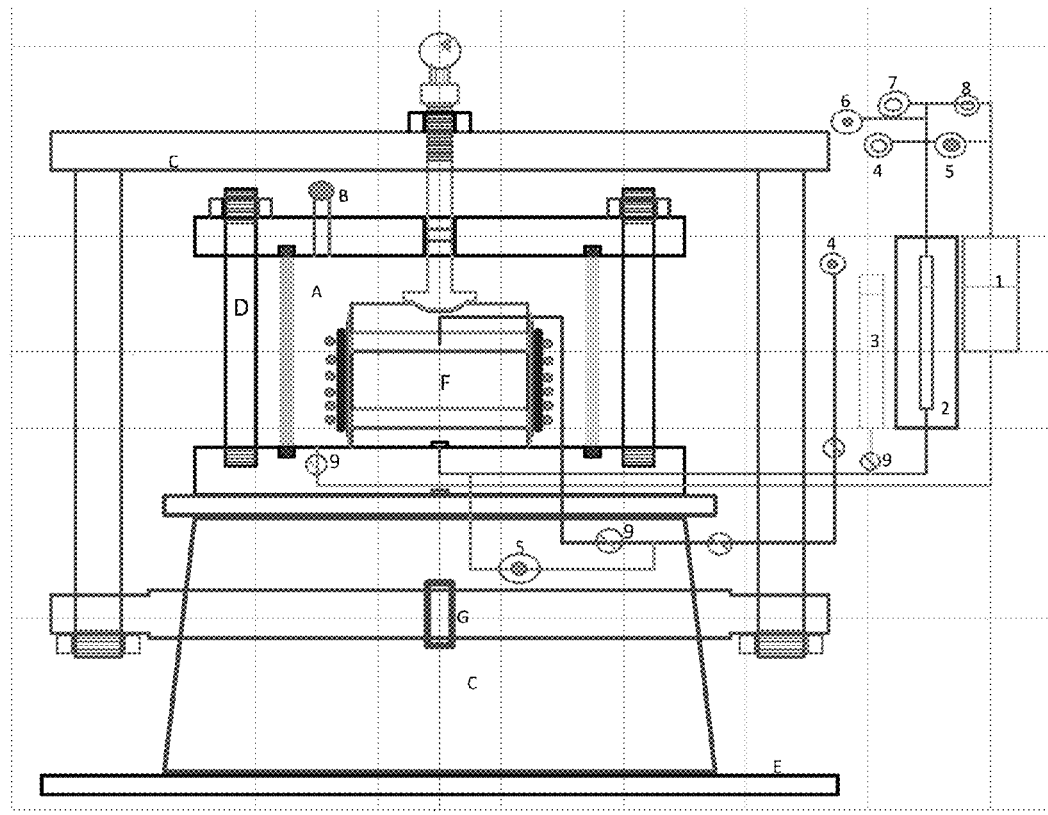

| For Control Panel | LEGEND |
|---|---|
| | For Chamber and Loading Device |
| 1 Chamber Pressure Reservoir | A Acrylic Chamber/Cell |
| 2 Volume Change Burette | B Vent |
| 3 Water Reservoir | C Incremental Loading Device/Frame |
| 4 Vacuum Regulator | D Clamping Rods for Chamber |
| 5 Differential Pressure Transducer | E Table Top |
| 6 Back Pressure Transducer | F 3-D Consolidation Test Sample Assembly |
| 7 Back Pressure Regulator | G Cantilever Loading Arm for weights |
| 8 Cell Pressure Regulator (Differential) | |
| 9 Valves | |

FIG. 16

TEST DEVICE FOR DETERMINING THREE-DIMENSIONAL CONSOLIDATION PROPERTIES OF SOILS

CROSS REFERENCE TO RELATED APPLICATIONS (IF ANY)

This specification is complete in itself.

STATEMENT OF FEDERALLY SPONSORED RESEARCH/DEVELOPMENT (IF ANY)

This invention is not sponsored or supported by federally sponsored research or development. This invention has been developed by me, Dr. Ramesh Chandra Gupta, Ph. D., P.E, President and Sole Owner of SAR6 INC., soley at my own cost and time.

The names of the parties to a joint research agreement if the claimed invention was made as a result of activities within the scope of a joint research agreement.

There is no joint research agreement with anyone. As stated earlier, this research/invention was conceived and completed solely by me (Dr. Ramesh C. Gupta, the inventor). It is my individual research work for this invention.

Reference to a "Sequence Listing," a table, or computer program listing appendix submitted on a compacted disc and incorporation by reference of the material on compact disc. The total number of compact disc including duplicates and the files on each compact disc shall be specified.

List of figures and tables with figure and table captions has been included in Item 8. The whole package is submitted in PDF format attached to the email. A compact disc containing the whole package can be submitted on demand from Patent Office.

BACKGROUND OF THE INVENTION

Standard test methods for determining one-dimensional consolidation properties of soils using incremental loading in accordance with ASTM D2435, or AASHTO 216 (2012) and of those of other international and organizations, do not accurately predict the consolidation properties of soils, such as values of vertical settlement, coefficients of consolidation in horizontal ($c_h$) and vertical directions ($c_v$), and modulus of elasticity (E); because fixed ring used in these tests do not allow horizontal displacement and dissipation of excess pore-water pressures in horizontal direction, whereas, in field, under application of a vertical load, both horizontal and vertical settlements occur along with dissipation of excess pore-water pressures in both vertical and horizontal directions. To overcome this more than 100 year old problem, the inventor (Dr. Ramesh Chandra Gupta, Ph. D., P.E.) has invented a test device for determining three-dimensional consolidation properties of soils, using a flexible ring which permits development of horizontal and vertical displacements, and dissipation of excess pore-water pressures in both horizontal and vertical directions, along with increased lateral resistance as takes place in field at any depth in a soil deposit when a vertical load is applied at the surface.

The flexible ring consists of filter fabric around the soil specimen, rubber membrane around the filter fabric, circular segmental metal plates around the membrane and elastomeric rubber bands or spring loaded jacket around the segmental plates to allow horizontal and vertical displacements, dissipation of excess pore-water pressures in horizontal and vertical directions, and increased lateral resistance with each increment of vertical load. Therefore, new test device, which simulates field condition, shall allow accurate determination of three-dimensional consolidation properties of soils (such as vertical and horizontal settlements, coefficients of consolidation ($c_v$ and $c_{hi}$) in horizontal and vertical directions, including three-dimensional coefficient of consolidation ($c_{3-D}$) and modulus of elasticity.

For this new test device, conventional incremental consolidation frame shall be used for applying vertical load increments, each to be maintained for 24 hours for allowing dissipation of excess pore-water pressures. Triaxial type chamber and loading system shall also be used after suitably modifying to adapt new 3-D consolidation device. With triaxial type chamber system or other sealed metal or acrylic systems, some modifications shall also be done to adapt to Incremental consolidation frame in place of triaxial loading system, to compare which is more suitable of these two loading systems for three-dimensional consolidation tests.

BRIEF SUMMARY OF THE INVENTION

This invention introduces a test device for determining three dimensional consolidation properties of soils using a flexible ring. The flexible ring consists of filter fabric around the soil specimen, rubber membrane around the filter fabric, circular segmental metal plates around the membrane and elastomeric rubber bands or rings or spring loaded jacket around the segmental plates to allow horizontal and vertical displacements, dissipation of excess pore-water pressures in horizontal and vertical directions, and increase in lateral resistance with each increment of vertical load. Therefore, new test device, which simulates field condition, shall allow accurate determination of three-dimensional consolidation properties of soils (including vertical and horizontal settlements, coefficients of consolidation ($c_v$ and $c_{hi}$) in horizontal and vertical directions and modulus of elasticity.

This is new invention for a test device to determine three-dimensional consolidation properties of soils. So far only one-dimensional consolidation properties have been determined using ASTM D2435 and AASHTO 216. One-dimensional consolidation devices, as shown in FIG. 1, do not simulate field conditions and therefore do not provide accurate values of consolidation properties.

Three-dimensional consolidation device consists of a flexible ring instead of a rigid ring as used for one-dimensional consolidation test. The flexible ring consists of about 10 stainless steel (or other non-corrodible metal) segment plates, circular arch in shape for 2.87" (72.9 mm) diameter specimen as shown in FIG. 2 through FIG. 5A. The thickness of plates may vary between 1/16" and 3/8" (1.6 mm and 9.53 mm) in thickness. Thicker segmental will not bend under the force exerted by elastomeric rubber bands or rings and in this respect may have some advantage over thinner plates. When vertical load is applied on soil specimen, vertical and horizontal displacement shall occur in the soil specimen, and the elastomeric rubber bands around the flexible ring shall expand to allow the horizontal displacement to occur.

FIG. 2 shows the schematic detail of a test when dissipation of excess pore water pressures can take place only in vertical direction, but unlike one-dimensional consolidation test, displacements both in vertical and horizontal (radial) directions can take place simultaneously when the vertical load is applied. This test shall permit the determination of coefficient of consolidation in vertical direction.

FIG. 3 shows the schematic detail of a test when dissipation of excess pore water pressures can take place only in horizontal (radial directions) direction, but unlike one-dimensional consolidation test, displacements both in vertical and horizontal (radial) directions can take place simultaneously when the vertical load is applied. This test shall permit the determination of coefficient of consolidation in horizontal direction. For this test, a filter fabric is wrapped around the soil specimen. A thick rubber membrane is then installed around the filter fabric. It may be noted that the filter fabric extends both below and top of the rubber membrane to allow dissipation of excess pore-water pressures. Porous discs are not required for this test as dissipation of pore-water pressures in vertical direction are not allowed in this test.

FIG. 4 shows the schematic detail of a test when dissipation of excess pore water pressures can take place both in vertical and horizontal (radial) directions, but unlike one-dimensional consolidation test, displacements both in vertical and horizontal (radial) directions can take place simultaneously when the vertical load is applied. This test shall permit the determination of three-dimensional coefficient of consolidation. In this test, three-dimensional consolidation shall take place exactly the same way as will take place in insitu conditions in the field. As shown in FIG. 4, porous discs are used to allow dissipation of pore-water pressures in vertical direction and filter fabric around soil specimen is used to allow dissipation of excess pore-water pressures in horizontal (radial) direction.

The specimens from various depths of a cohesive deposit are obtained by use of Shelby tubes or other type of samplers. The sample shall be extracted from the samplers, in the same manner as is used to extract samples for one-dimensional consolidation test. For the three-dimensional consolidation tests using flexible ring, there is no need of shaping the specimen to push into fixed ring as is required for the one-dimensional consolidation test. After cutting to the required lengths and leveling the ends of the specimen, the specimen for three-dimensional consolidation test, shall be placed on the porous disc/base plate and then capped by top porous disc/loading head. Using a membrane expander, filter consisting of elastic filter fabric in the form a cylinder shall be installed around the soil specimen as is shown in FIG. 3 and FIG. 4. Using membrane expander, a thick rubber membrane shall be installed around the filter fabric/soil specimen as shown in FIG. 3 and FIG. 4. A thicker rubber membrane which can be installed using a membrane expander or other appropriate device, shall have some advantage over thinner membrane as a thick rubber membrane shall keep cylindrical shape along the joint space between the segment plates. It may be noted that filter fabric is not needed for test which allows dissipation of excess pore-water pressures in vertical direction only, as shown in FIG. 2.

Commercially available woven or non-woven filter fabric can also be used after stitching it into a cylindrical shape using a strip of elastic cloth. Filter fabric can also be wrapped around the soil specimen with about ½" (12.7 mm) overlap and maintained stretched or taut in place by a 1" (25.4 mm) long adhesive tape at the ends. This tape shall be removed after installation of the rubber membrane around the specimen. Stainless steel segment plates or non-corrodible metal segment plates of thickness generally varying between about 1/16" and 3/8" (1.59 and 9.53 mm) are installed around the membrane, using two half-circular brackets as shown in FIG. 5A and FIG. 5B. The width of the bracket plates may generally vary between about 3/8" and 1" (9.53 mm and 25.4 mm). The thickness of these brackets can vary generally between about 3/32" and 3/8" (2.38 mm and 9.53 mm). Elastomeric rubber bands of generally about between 1/16 and 3/16" (1.6 mm and 4.76 mm) thickness are slipped on around the plates at marked locations as shown in FIG. 7. The width of rubber bands can vary generally between about 1/8" and ½" (3.2 mm and 12.7 mm). The diameter of elastomeric rubber rings with circular cross-section, when used in place of bands, can vary generally between about 1/16" and 3/8" (between 1.6 and 9.53 mm). Several threaded holes at different heights of the plates in addition to those shown in figures, shall also be provided to install the brackets at different heights. For example, as an alternative, after rubber bands or rings above the bracket have already been installed, another bracket can be installed near the bottom of the segmented plates, thereafter, the bracket at the middle of the segmented plates can be un-installed, and rubber bands or rings are then installed in the remaining space above the bracket.

The brackets are then un-installed. Remaining rubber bands or rings are slipped on around the plates in the space earlier covered by the brackets, as shown in FIG. 8. The expandable or flexible ring has thus been installed around the soil specimen. Since segmental circular plates are resting against the top and bottom porous discs or base plate and loading head, initially the lateral load exerted by rubber bands acts on the porous discs and very little, if any, directly on the soil specimen in the beginning of the test. When specimen begins to undergo lateral displacement or lateral expansion during the test, the rubber bands around the segmental plates shall stretch and exert pressure on the segmental plates thereby on the surface of the soil specimen all along its height and shall help in maintaining the uniform diameter through its height during the test; the plates are then not in contact with porous discs and so rubber bands exert lateral pressure on the specimen. As many rubber bands as needed to maintain uniform diameter of cylindrical specimen and also to resist lateral pressures proportional to the applied vertical load during the test, shall be used. The inside surface of segment plates shall be lubricated to reduce friction between rubber membrane around soil specimen and the plates. The function of segmental stainless steel plates is to uniformly distribute the lateral load applied by rubber bands on the soil specimen.

Alternatively, the lubricated segment plates can be assembled around soil specimen by use of about between ½" and 1" (12.7 mm and 25.4 mm) wide leather or nylon or polyester or polypropylene VELCRO straps. First, segment plates are fastened to VELCRO strap using 5-44 or M-3 screws as shown in FIG. 9 (other screw sizes may be used along with appropriate female threads in segment plates). Then the assembled plates are wrapped around the soil specimen and maintained in position by VELCRO strap as shown in FIG. 10. The rubber bands of thickness of generally between about 1/16" and 3/16" (1.59 mm and 4.76 mm) are slipped on around the plates as shown in FIG. 11. The screws are unthreaded to remove the straps. The remaining rubber bands are then slipped on around the plates in the space earlier occupied by the VELCRO straps, as shown in FIG. 12A. The flexible ring has now been installed around the soil specimen. The leather or nylon VELCRO straps can also be installed near the bottom in addition shown one shown at middle of the height in the figures as considered necessary to properly install the rubber bands or rings.

Sizes of segment plates, half brackets and rubber bands shown in FIG. 2 through FIG. 9 and described in the text above are based on soil specimen diameter of 2.87" (72.9 mm) in diameter. Diameter of soil specimen is also dependent on inside diameter of Shelby tubes or other type of samplers used for extracting the samples from a cohesive deposit. Inside diameter of Shelby tubes as per ASTM standards are 1.905" (48.42 mm), 2.87" (72.9 mm) and 4.76" (120.9 mm). The diameter of circular arch shaped segment plates and two half brackets shall depend on the diameter soil specimen. Number of segment plates shall be generally about 8, 10 and 16 for soil specimen of 1.905" (48.42 mm), 2.87" (72.9 mm) and 4.76" (120.9 mm), respectively. For other specimen sizes, special design detail shall be used.

FIG. 13 shows the calibration device. In FIG. 14, the flexible ring has been mounted around the calibration device for performing calibration of flexible ring to determine the hydraulic pressure or water overhead above calibration device versus lateral strain relationship and thereby to determine combined modulus of elasticity of filter fabric, rubber membrane and elastomeric rubber membrane.

The details as described here-in for flexible ring including its installation techniques, instrumentation and calibration device may be revised in future, when there is a need to do so for improving the accuracy and workability of the test device for determination of three-dimensional consolidation properties of soils.

In FIG. 15 and FIG. 16, the detail shows 3-D device assembly placed in a triaxial chamber with triaxial type loading system and incremental loading system, respectively. FIG. 17 shows the LVDT or strain gage mounted U-Frame device resting on frictionless bearings to allow radial expansion of the specimen during the test.

BRIEF DESCRIPTION OF THE SEVERAL VIEWS OF THE DRAWING

FIG. 5A and FIG. 5B show schematic plan view detail of installing circular segment plates around the soil specimen using two half-circular brackets. FIG. 5C shows the joint detail where bracket plates of the two-half brackets are screwed together.

FIG. 12A shows an elevation view of installation of the reservoir cylindrical wall made of stainless steel or of Acrylic or Perspex. At the base, the reservoir cylindrical wall is clamped to the table top using a rubber gasket for water tightness and appropriate size screws. FIG. 12B shows another detail of a reservoir for placing assembled 3-D device in it. In this case reservoir cylindrical wall and bottom plate consists either of metal or acrylic. When acrylic is used, the acrylic wall and the bottom shall be connected by weld-on plastic adhesive. In case of metal, normal weld shall be used. FIG. 12C shows that instead of weld, the acrylic or metal tube shall be screwed in the base plate, when 3-D device has already been assembled on base plate.

FIG. 12D shows a sealed chamber which can withstand lateral water pressure at least up to 150 psi (1034 kPa). For this chamber, first 3-D device shall be assembled on the metal base plate, then the side metal wall shall be installed and bolted to the base plate as shown in this figure. The O-ring or flat gasket shall seal the base plate and top plate to the cylindrical side walls.

FIG. 12E shows another schematic detail of a sealed metal or acrylic chamber. For this detail a thick metal or acrylic cylindrical wall shall be used in which the holes can be drilled as shown in this figure. The long bolts shall be inserted in the holes from the bottom and tightened from the top when top plate has been placed. Both bottom and top plates shall be made watertight by seating a flat gasket or O-Rings/Ring in between the plates and the side wall.

FIG. 15 shows schematic detail for assembling a 3-D consolidation test device on base plate then covered by a triaxial type chamber and also connected to control panel and load frame to perform the test.

FIG. 16 shows schematic detail for assembling a 3-D consolidation test device on base plate then covered by a triaxial type chamber and also connected to control panel and incremental loading device/frame to perform the test.

FIGURE AND TABLE CAPTIONS ARE GIVEN BELOW

Figure 1:
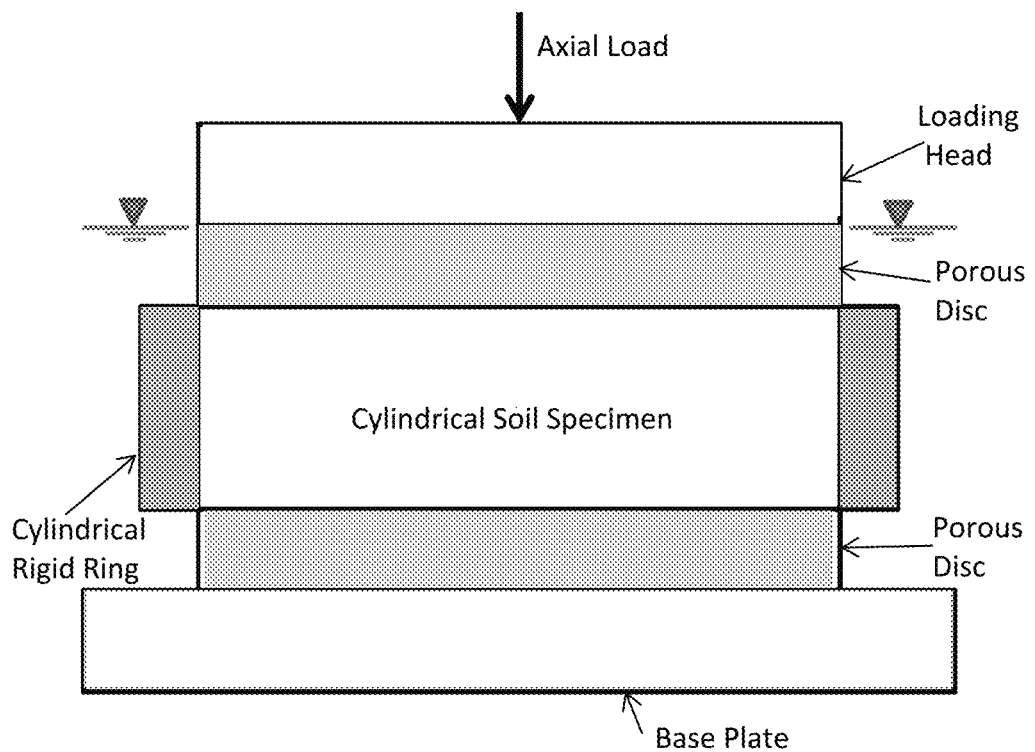
FIG. 1 describes the test device for determining one-dimensional consolidation properties of soils.

FIG. 1: Schematic detail of test device for performing one-dimensional consolidation test.

Figure 2:
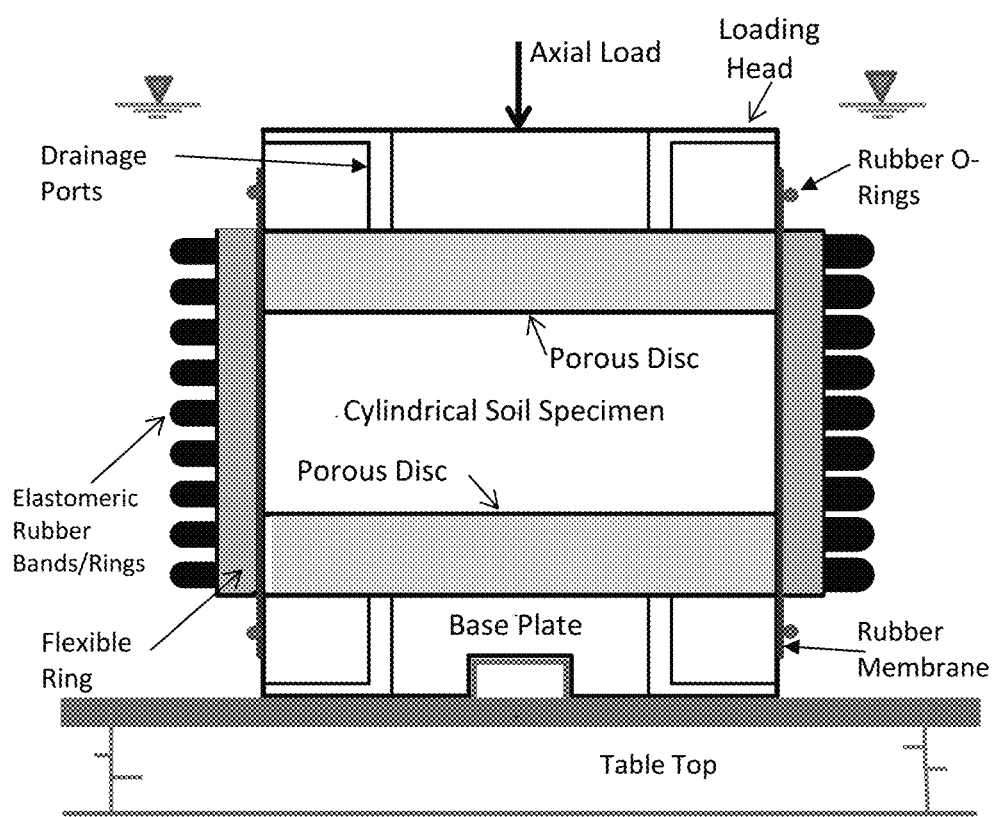
FIG. 2 shows three-dimensional test device permitting both horizontal and lateral displacement but allowing dissipation of excess pore-water pressures only vertical direction.

FIG. 2: Schematic Detail of three dimensional test device for permitting dissipation of excess pore-water pressure in vertical direction only, but allowing vertical and horizontal displacement of the soil specimen to take place.

Figure 3:
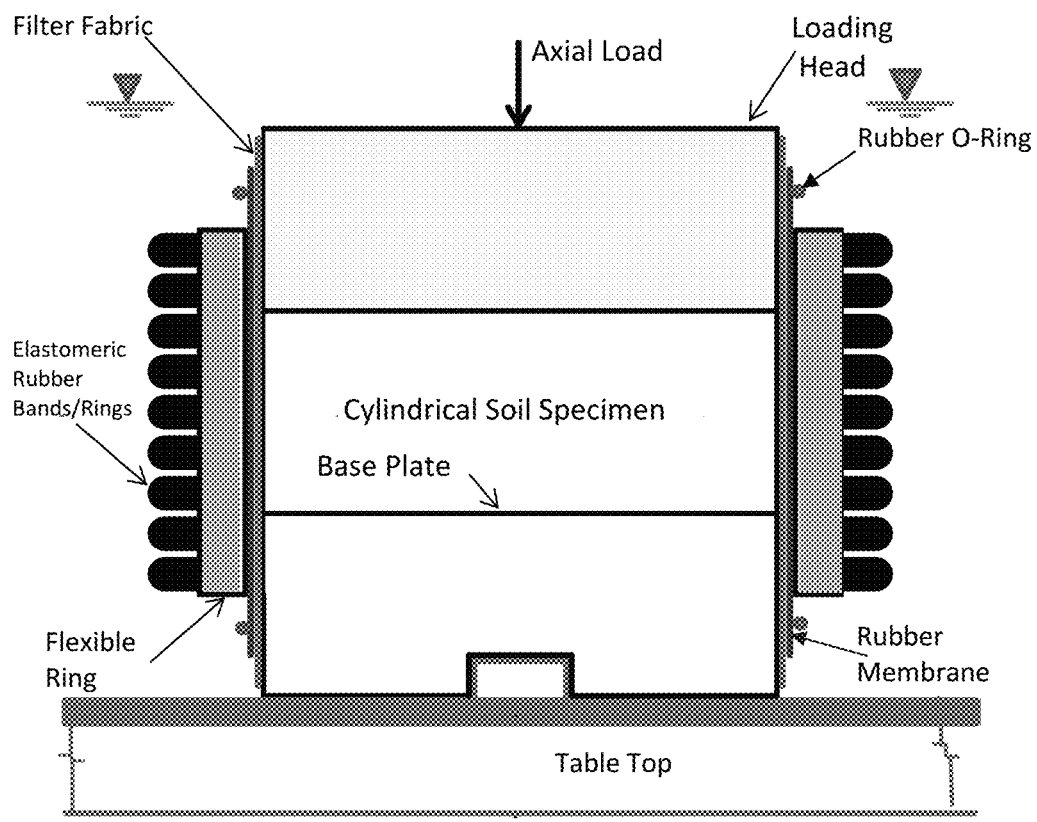
FIG. 3 shows three-dimensional test device permitting both horizontal and lateral displacement but allowing dissipation of excess pore-water pressures only horizontal (radial) direction.

FIG. 3: Schematic Detail of three dimensional test device for permitting dissipation of excess pore-water pressure in horizontal direction only, but allowing vertical and horizontal displacements of the soil specimen to take place.

Figure 4:
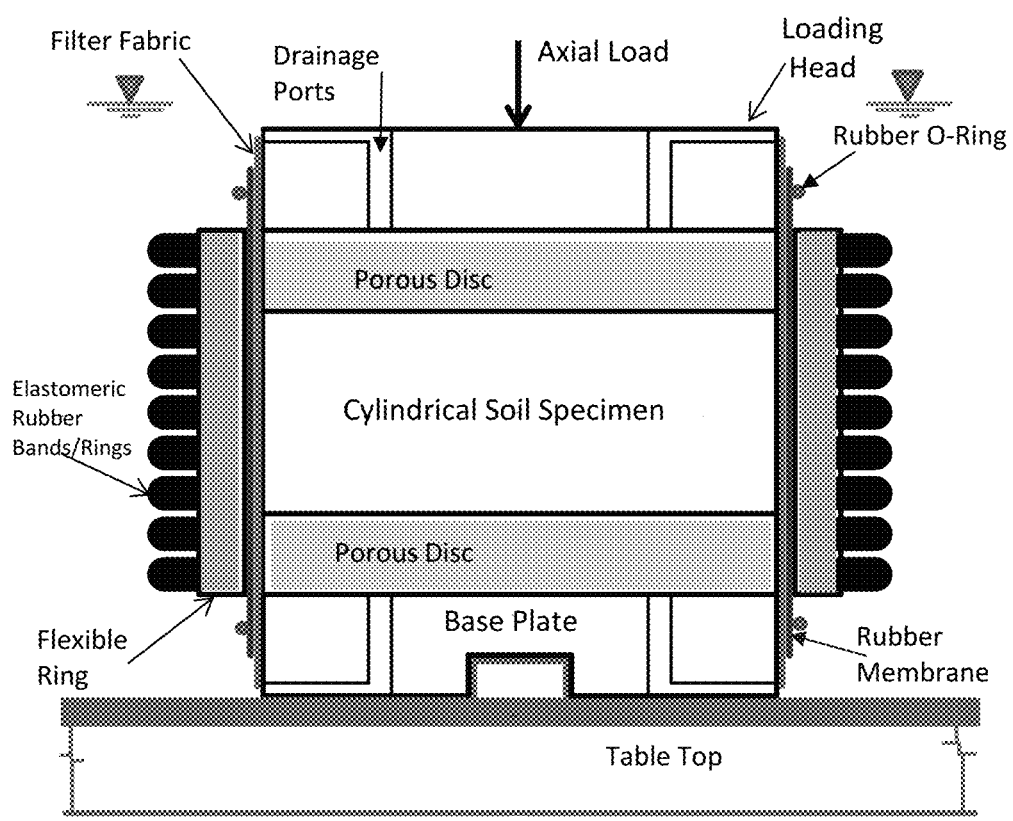
FIG. 4 shows three-dimensional consolidation device permitting both horizontal and lateral displacement and also allowing dissipation of excess pore-water pressures both horizontal and vertical directions.

FIG. 4: Schematic detail of three dimensional consolidation test device for permitting dissipation of excess pore-water pressure in vertical and horizontal directions, and also allowing vertical and horizontal displacements of the soil specimen to take place.

FIG. 5A and FIG. 5B: Layout plan for installation of circular segment plates around soil specimen using two half-circular brackets. FIG. 5C: Joint detail where bracket plates of the two-half brackets are screwed together.

Figure 6:
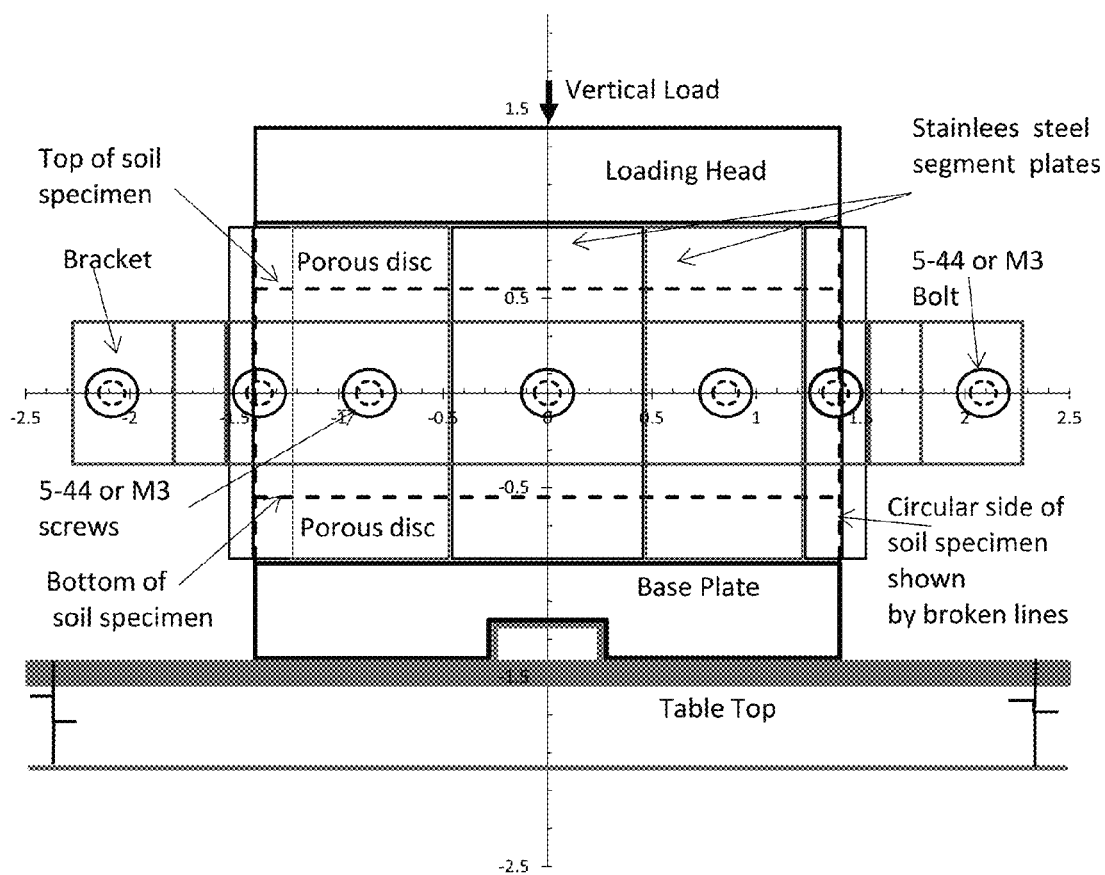
FIG. 6 shows schematic elevation view detail of installing circular segment plates around the soil specimen using two half-circular brackets.

FIG. 6: Elevation view for installation of circular segment plates around soil specimen using two half-circular brackets.

Figure 7:
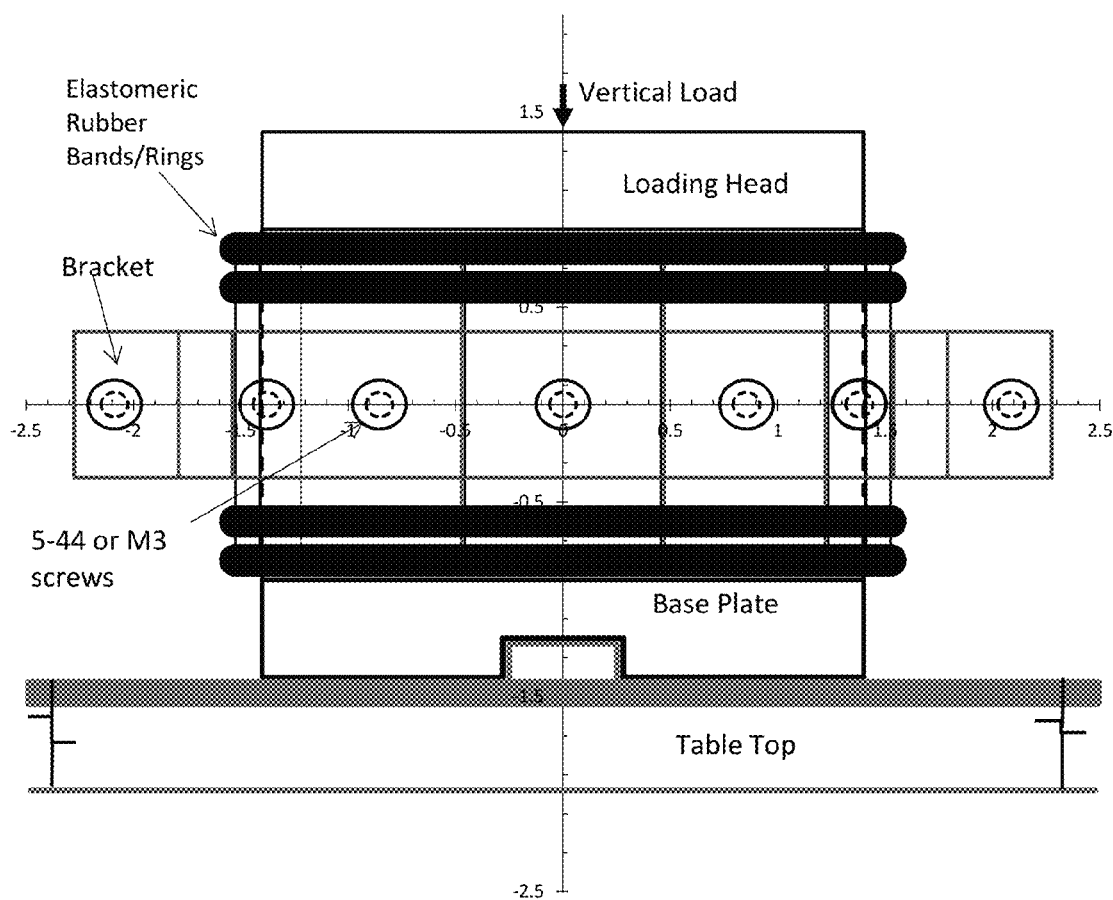
FIG. 7 shows the elevation view when elastomeric rubber bands have been slipped above and below the two half-circular brackets.

FIG. 7: Elevation view for installation of rubber bands around circular segment plates in the space above and/or below half-circular brackets.

Figure 8:
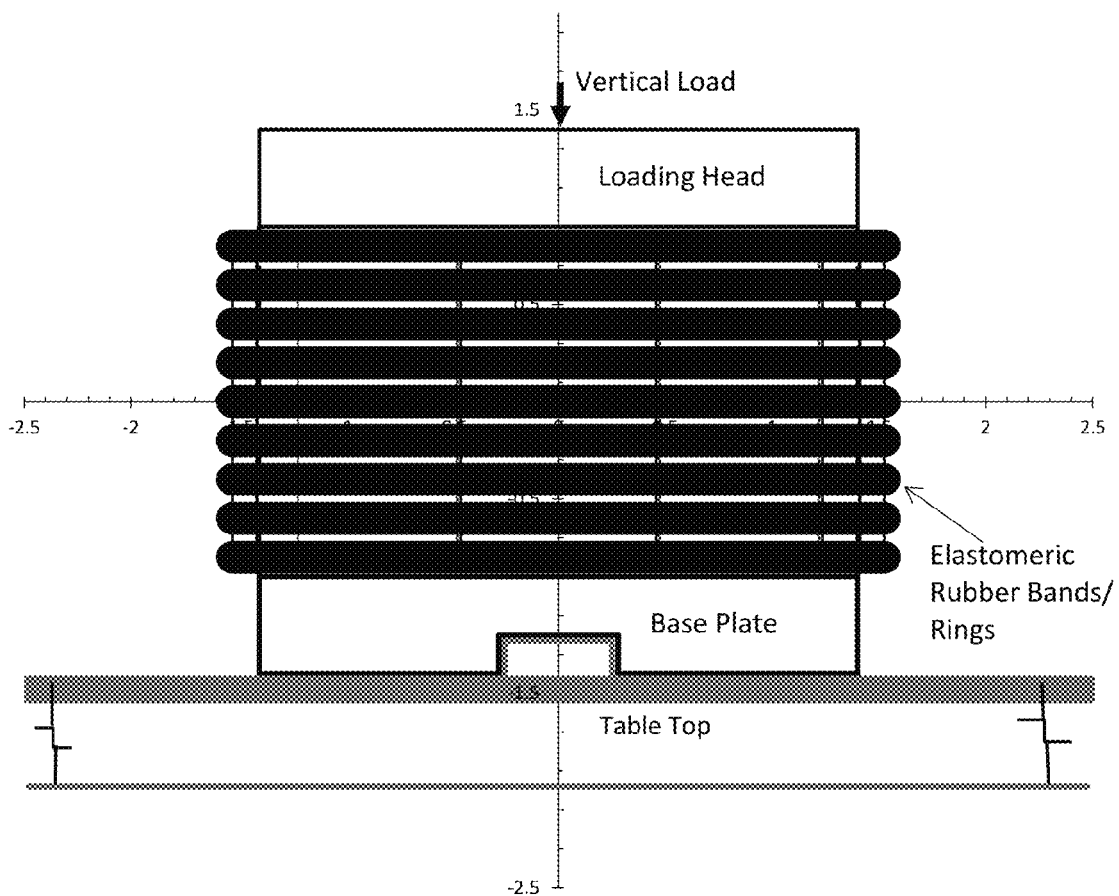
FIG. 8 shows the elevation view when both half-circular brackets have been un-installed and remaining rubber bands in the area previously occupied by brackets have been installed.

FIG. 8: Elevation view for installation of additional rubber bands around circular segment plates in the remaining space after un-installing half-circular brackets.

Figure 9:
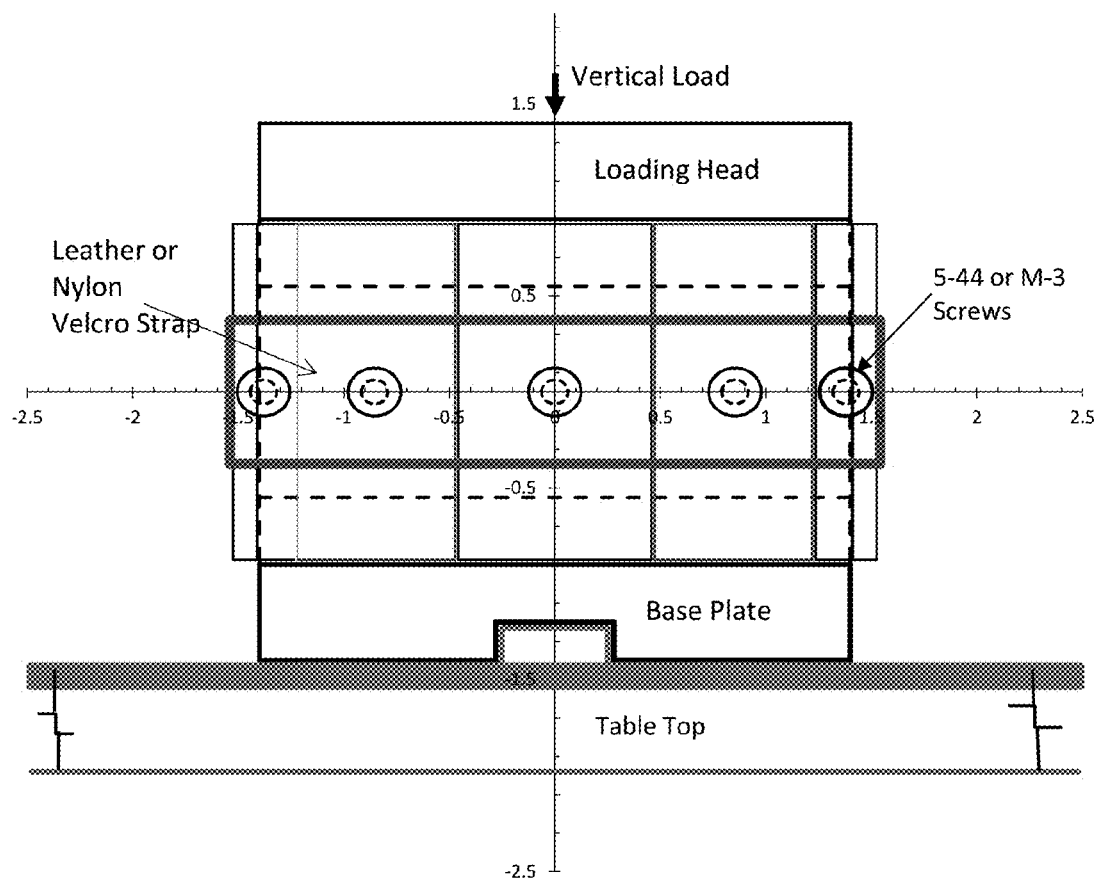
FIG. 9 shows the installation of circular segment plates using leather or nylon VELCRO straps, instead of using two half-circular brackets.

FIG. 9: Elevation view for installation of circular segment plates around soil specimen using leather or nylon VELCRO strap.

Figure 10:
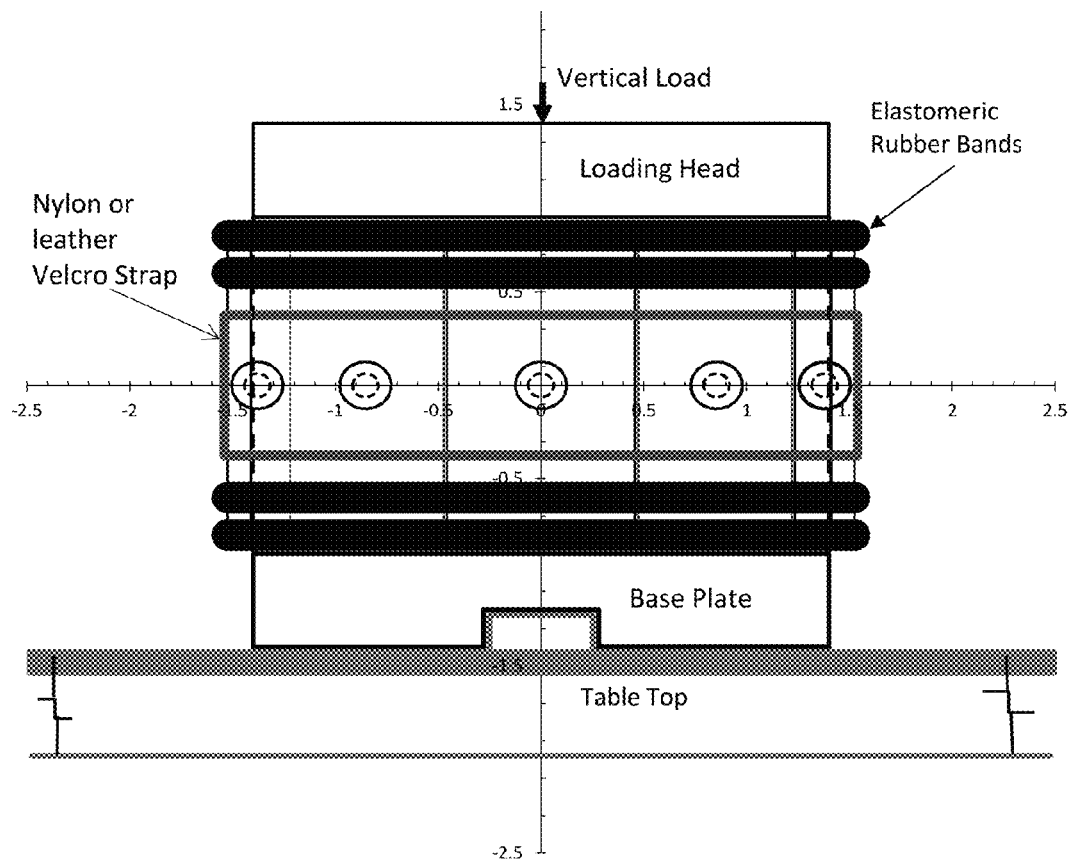
FIG. 10 shows the elevation view when elastomeric rubber bands have been slipped above and/or below and above the VELCRO straps.

FIG. 10: Elevation view for installation of rubber bands around circular segment plates in the space above and/or below VELCRO strap.

Figure 11:
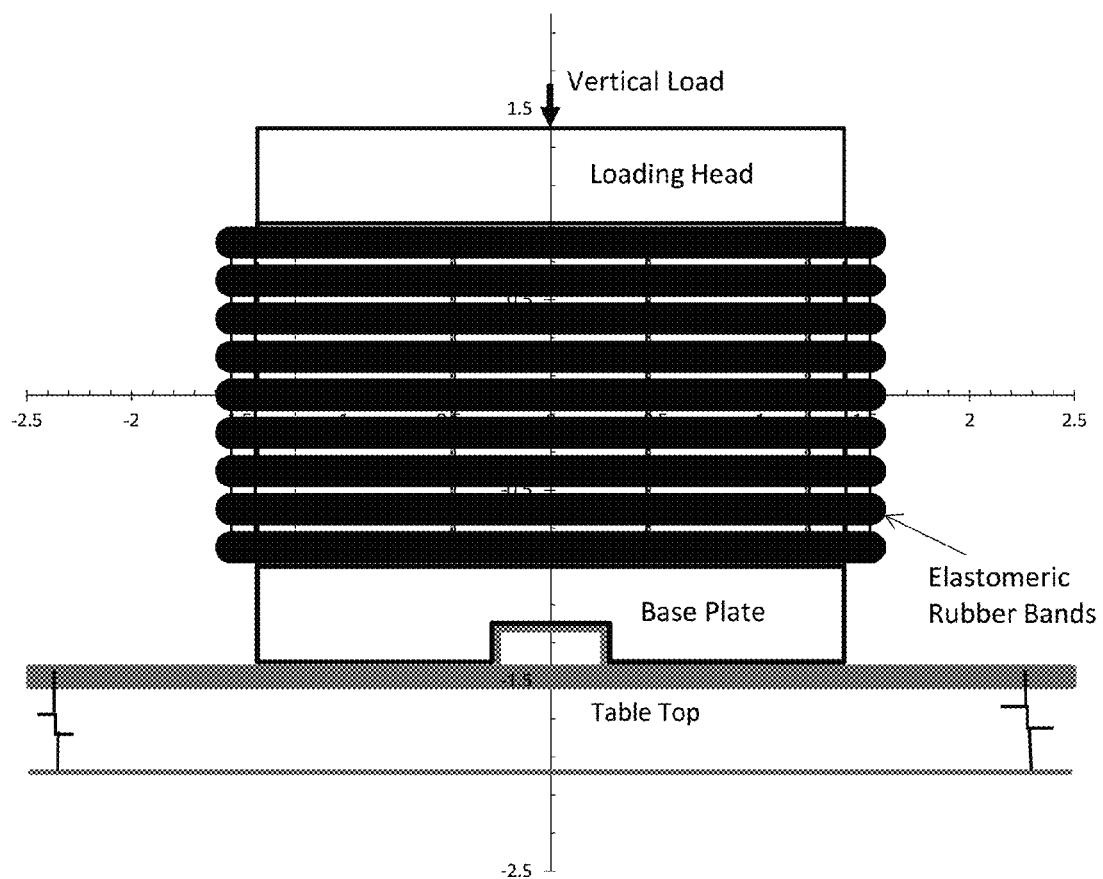
FIG. 11 shows the elevation view when VELCRO strap has been un-installed and remaining rubber bands in the area previously occupied by brackets have been installed. Thus installation of flexible ring using VELCRO straps has been completed.

FIG. 11: Elevation view for installation of additional rubber bands around circular segment plates after un-installing VELCRO strap.

FIG. 12A: Elevation view of three-dimensional consolidation test device after installation of cylindrical reservoir wall and then filling water in the reservoir, FIG. 12B: open reservoir consisting of acrylic or metal wall and bottom welded together.

FIG. 12C: open reservoir consisting of metal or acrylic wall and bottom threaded together.

FIG. 12D: water tight metal chamber/reservoir with separate bolts at bottom and top to seal plates to cylindrical side wall for application of lateral pressure in the chamber.

FIG. 12E water tight metal or acrylic chamber/reservoir with long bolts inside holes in a thick cylindrical wall for sealing bottom and top plates to cylindrical side wall for application of lateral pressure in the chamber.

Figure 13:
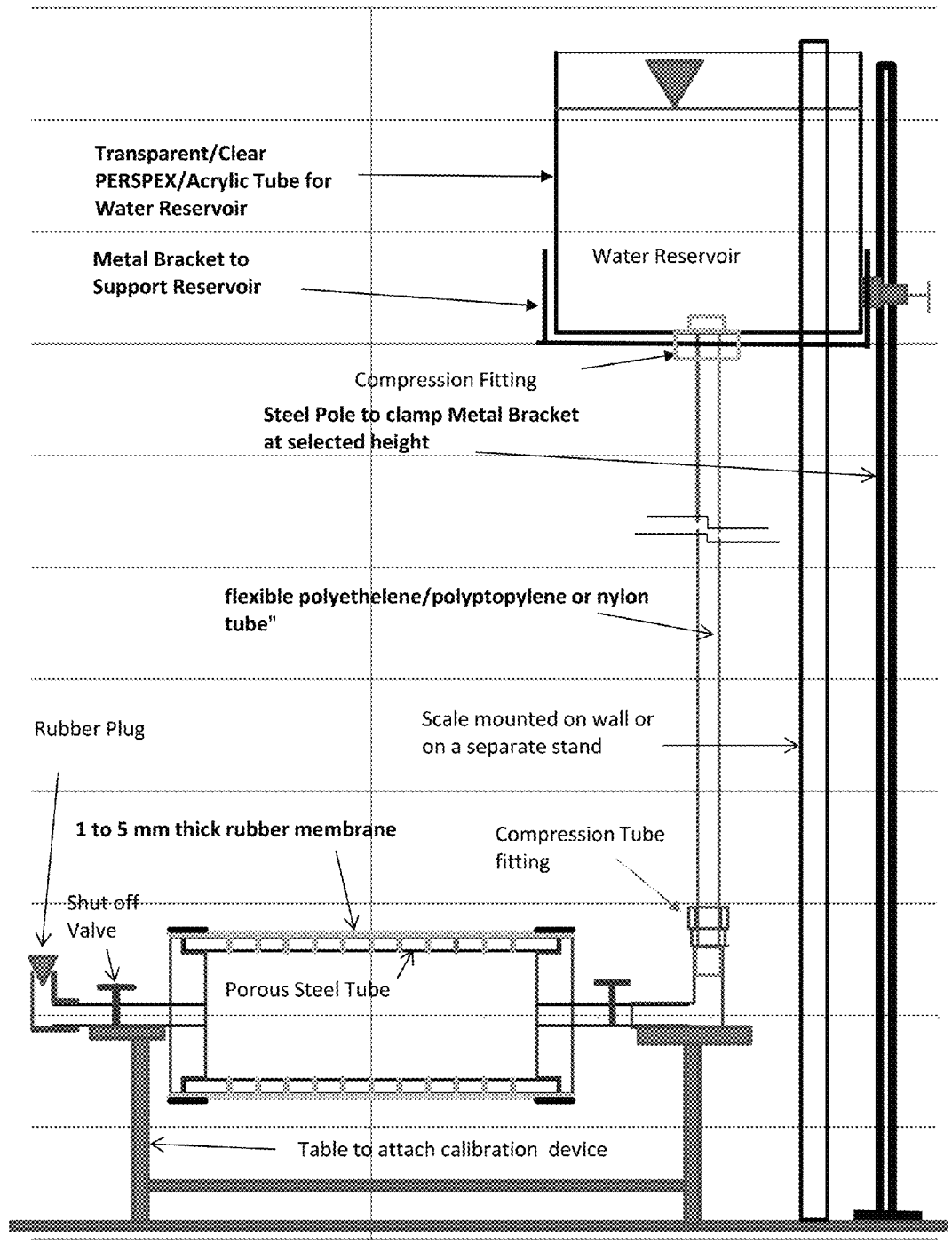
FIG. 13 shows the calibration device, which consists of porous metal tube covered by a rubber membrane. The tube is connected to a reservoir which can be raised or lowered on a metal stand.

FIG. 13: Elevation view of calibration device.

Figure 14:
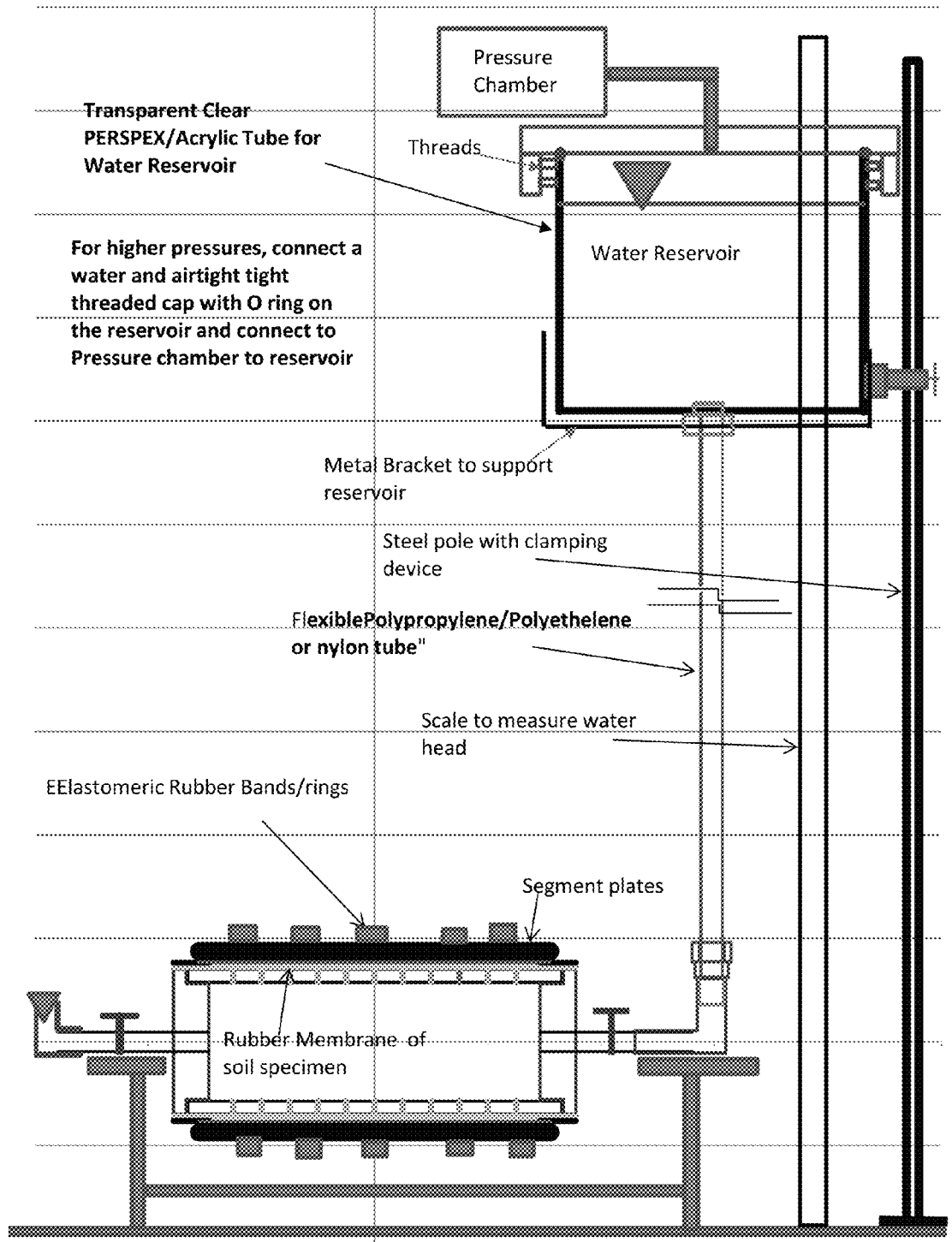
In FIG. 14, the flexible ring has been mounted around the calibration device for performing calibration of flexible ring to determine the hydraulic pressure versus lateral strain relationship and thereby to determine combined modulus of elasticity of filter fabric, rubber membrane and elastomeric rubber membrane.

FIG. 14: Elevation view of the calibration device after installation of flexible ring for performing its calibration.

FIG. 15: Sectional elevation of 3-D consolidation device setup with triaxial type loading system and water chamber with control panel to apply lateral pressure on soil specimen.

FIG. 16: Sectional elevation of 3-D consolidation device setup with incremental consolidation loading system and water chamber with control panel to apply lateral pressure on soil specimen.

Figure 17:
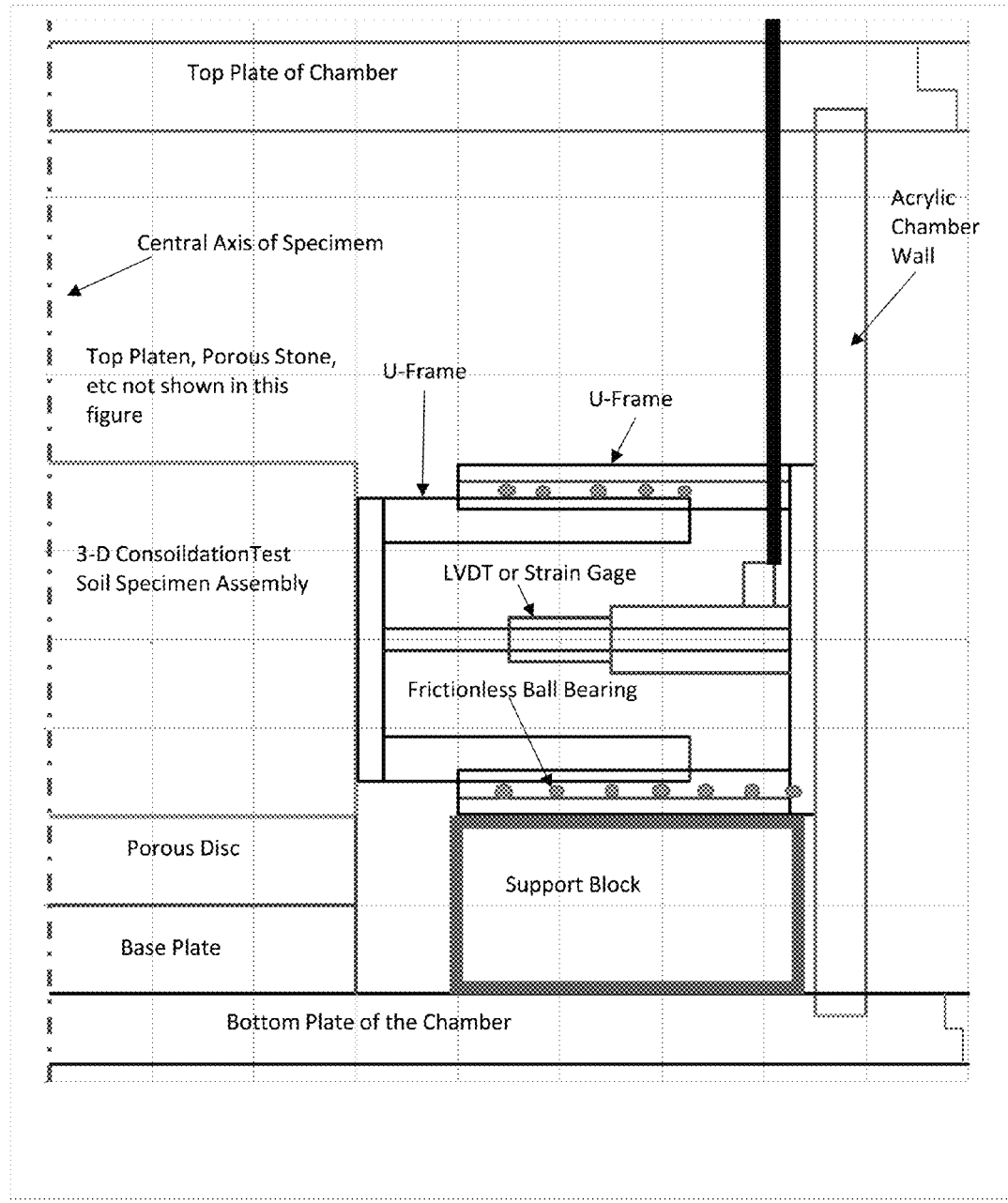
FIG. 17 shows the frictionless U-Frame device to mount LVDT or strain gage to measure radial expansion of specimen.

FIG. 17: Frictionless U-Frame for mounting LVDT or strain Gage to measure radial expansion of the sample.

Table 1: Form for entering data to calibrate the calibration device

Table 2: Form for entering data to calibrate the flexible ring

DETAILED DESCRIPTION OF THE INVENTION

Detailed description of the invention has been explained below in Sections (a) though (g).

(a) Standard Test Methods and their Limitations

The standard test method for one-dimensional consolidation properties of soils using incremental loading is described in ASTM Designation: D2435/D2435M-11 and in AASHTO 216. International and national organizations of several countries have their own standards for this test. The test apparatus consists of a rigid ring as shown in FIG. 1. The soil specimen is pushed in the ring to perform the test.

When foundation loads are transmitted to cohesive subsoils, there is a tendency for a volumetric strain which in the case of saturated material is manifested in an increase in pore water pressure. With sufficient elapsed time, water flows out of the soil pores, permitting excess pore-water pressure to dissipate. The analysis of the volumetric strains which result, and the vertical settlements accompanying them, is simplified if we assume that such strains occur only in vertical direction. Such an assumption may not be unreasonable when the geometric and boundary conditions in the field are such that vertical strains dominate. For example, when dimensions of the loaded area are large relative to the thickness of the compressible stratum and/or when the compressible material lies between two stiffer soils whose presence tends to reduce the magnitude of horizontal strains, an approximately one-dimensional compression of the soil will occur (Perloff and Baron, 1976).

However, generally, the above mentioned example rarely occurs. In most cases, three-dimensional consolidation and settlements occur. Therefore, volumetric strains in soils significantly depend on displacements both in vertical and horizontal or radial directions. In those cases, in which the thickness of compressible strata is large related to the loaded area, the three dimensional nature of the problem shall influence the magnitude and rate of settlement. Although numerical analysis methods offer the prospect of rational consideration of three-dimensional compression effects, they have not proven useful in practice (Winterkorn and Fang, 1990). In view of this, semi-empirical approaches have been used for estimating three-dimensional consolidation properties. The most commonly applied method was developed by Skempton and Bjerrum (1957), using two assumptions: (1) even though the induced excess pore water results from three-dimensional effects, the settlements are assumed as one-dimensional, (2) to account for three-dimensional consolidation, the vertical settlement at the centerline is predicted as equal to product of one-dimensional consolidation settlement times a factor $\lambda$. The value of $\lambda$ is estimated using a chart, which has been plotted based on overconsolidation ratio and ratio of the width of foundation with thickness of consolidating stratum (HRB, 1973).

The coefficients of permeability and consolidation in horizontal direction has been found to be much greater than the coefficients of permeability and consolidation in vertical direction of the same soil deposits or stratum (Terzaghi et al. 1996). Depending on the anisotropy of the soil deposits or presence of very thin sand/silt layers in the soil deposits, the coefficients of permeability and consolidation in horizontal direction could be even 10 times greater than the coefficients of permeability and consolidation in vertical direction. In such cases, the method of Skempton and Bjerrum (1957) using factor cannot be applied.

In view of the above, it is very important to develop a test which can determine the three-dimensional consolidation properties of soil deposits. To solve this problem of more than 100 years, the inventor has invented a three-dimensional consolidation test device which permits the dissipation of excess pore water pressure both in vertical and horizontal (radial directions) directions along with settlements occurring both in vertical and horizontal (radial) directions.

(b) Three-Dimensional Consolidation Test Device

Three-dimensional consolidation device consists of a flexible ring instead of a rigid ring as used for one-dimensional consolidation test. The flexible ring consists of about 10 stainless steel segment plates, circular arch in shape for 2.87" (72.9 mm) diameter specimen as shown in FIG. 2 through FIG. 5A and FIG. 5B. The thickness of plates may vary generally between about 1/16" and 3/8" (1.59 mm and 9.53 mm) in thickness. Thicker segmental plates will not bend under the force exerted by elastomeric rubber bands and in this respect may have some advantage over thinner plates. When vertical load is applied on soil specimen, vertical and horizontal displacement shall occur in the soil specimen, the elastomeric rubber bands around the flexible ring shall expand to allow the horizontal displacement to occur uniformly.

FIG. 2 shows the schematic detail of a test when dissipation of excess pore water pressures can take place only in vertical direction, but unlike one-dimensional consolidation test, displacements both in vertical and horizontal (radial) directions can take place simultaneously when the vertical load is applied. This test shall permit the determination of coefficient of consolidation in vertical direction.

FIG. 3 shows the schematic detail of a test when dissipation of excess pore water pressures can take place only in horizontal (radial directions) direction, but unlike one-dimensional consolidation test, displacements both in vertical and horizontal (radial) directions can take place simultaneously when the vertical load is applied. This test shall permit the determination of coefficient of consolidation in horizontal direction. For this test, a filter fabric is wrapped around the soil specimen. A thick rubber membrane is then installed around the filter fabric. It may be noted that the filter fabric extends both below and top of the rubber membrane to allow dissipation of pore water pressures. Porous discs are not required for this test as dissipation of pore-water pressures in vertical direction is not allowed in this test.

FIG. 4 shows the schematic detail of a test when dissipation of excess pore water pressures can take place both in vertical and horizontal (radial) directions, but unlike one-dimensional consolidation test, displacements both in vertical and horizontal (radial) directions can also take place simultaneously when the vertical load is applied. This test shall permit the determination of three-dimensional coefficient of consolidation. In this test, three-dimensional consolidation shall take place exactly the same way as will take place in insitu conditions in the field. As shown in FIG. 4, porous discs are used to allow dissipation of pore-water pressures in vertical direction and filter fabric around soil specimen is used to allow dissipation of excess pore-water pressures in horizontal (radial) direction.

If the field conditions are such that the drainage boundary is only at the top of the soil deposit and not below it, then the porous disc at the bottom shall be replaced by metal plate with no drainage port in it.

If the field conditions are such that the drainage boundary is only at the bottom of the soil deposit and not above it, then the porous disc at the top shall be replaced by metal plate with no drainage port in it.

All these three type of tests shall be performed on the soil specimen extracted preferably from the same Shelby tube, or from the same soil strata. The test setup shown in FIG. 4 shall be used to determine three-dimensional coefficient of consolidation. These tests shall also allow to develop correlations to determine three-dimensional coefficient of consolidation when coefficient of consolidation in vertical direction using test setup shown in FIG. 2 and coefficient of consolidation in horizontal direction using test setup shown in FIG. 3 have been determined. Time rate of settlement both in vertical and horizontal directions and rate of volume change of a soil deposit can be accurately determined from the results available from these tests. Numerical analyses such as finite element or finite difference analyses based on the results of these consolidation tests can then be made accurately to determine the volume change, rate of volume change with time, horizontal and vertical displacement, rates of horizontal and vertical displacements with time, and rate of increase in vertical and horizontal stresses with time, and rate of dissipation of excess pore-water pressures, in each and every single small soil element of soil deposit using appropriate soil element matrix, thereby for the whole soil deposit, under influence of the load at the surface.

(c) Installation Details for the Three-Dimensional Consolidation Test Device

The specimens from various depths of a cohesive deposit are obtained by use of Shelby tubes or other type of samplers. The sample shall be extracted from the samplers, in the same manner as is used to extract samples for one-dimensional consolidation test. For the three-dimensional consolidation tests using flexible ring, there is no need of shaping the specimen to push into fixed ring as is required for the one-dimensional consolidation test. After cutting to the required lengths and leveling the ends of the specimen, the specimen for three-dimensional consolidation test, shall be placed on the porous disc/base plate and then capped by top porous disc/loading head. Using a membrane expander, filter consisting of elastic filter fabric in the form a cylinder shall be installed around the soil specimen as is shown in FIG. 3 and FIG. 4. Using membrane expander, a thick rubber membrane shall be installed around the filter fabric/soil specimen as shown in FIG. 3 and FIG. 4. A thicker rubber membrane which can be installed using a membrane expander or other appropriate device, shall have some advantage over thinner membrane as a thick rubber membrane shall keep cylindrical shape along the joint space between the segment plates. It may be noted that filter fabric is not needed for test which allows dissipation of excess pore-water pressures in vertical direction only, as shown in FIG. 2.

Commercially available woven or non-woven filter fabric can also be used after stitching it into a cylindrical shape using a strip of elastic cloth. Filter fabric can also be wrapped around the soil specimen with approximately about ½" (12.7 mm) overlap and maintained stretched or taut in place by about a 1" long adhesive tape at the ends. This tape shall be removed after installation of the rubber membrane around the specimen. Stainless steel segment plates or non-corrodible metal segment plates of thickness generally varying between about 1/16" and 3/8" (1.59 and 9.53 mm) are installed around the membrane, using two half-circular brackets as shown in FIG. 5A and FIG. 5B. The width of the bracket plates may generally vary between about 3/8" and 1" (9.53 mm and 25.4 mm). The thickness of these brackets can vary generally between about 3/32" and 3/8" (2.38 mm and 9.53 mm). Screw sizes other than those given in figures may be used along with appropriate female threads in segment plates. Elastomeric rubber bands of thickness of generally between 1/16" and 3/16" (1.59 and 4.76 mm) are slipped on around the plates at marked locations as shown in FIG. 7. The width of rubber bands can vary generally between about 1/8" and ½" (3.2 mm and 12.7 mm). The diameter of elastomeric rubber rings with circular cross-section, when used in place of bands, can vary generally between about 1/16" and 3/8" (between 1.6 and 9.53 mm). Several threaded holes at different heights of the plates in addition to those shown in figures, shall also be provided in the plates to install the brackets at different heights. For example, as an alternative, after rubber bands or rings above the bracket has already been installed, another bracket can be installed near the bottom of the segmented plates, thereafter, the bracket at the middle of the segmented plates can be un-installed, and rubber bands or rings are then installed in the remaining space above the bracket. Similar details for installation of segmental plates with threaded holes at various heights, and also for bracket and rubber rings/bands can also be used for expandable jackets around triaxial test specimen.

The brackets are then un-installed. Remaining rubber bands or rings are slipped on around the plates in the space earlier covered by the bracket, as shown in FIG. 8. The expandable or flexible ring has thus been installed around the soil specimen. Since segmental circular plates are resting against the top and bottom porous discs or base plate and loading head, initially the lateral load exerted by rubber bands acts on the porous discs and very little, if any, directly on the soil specimen in the beginning of the test. When specimen begins to undergo lateral displacement or lateral expansion during the test, the rubber bands around the segmental plates shall stretch and exert pressure on the segmental plates thereby on the surface of the soil specimen all along its height and shall help in maintaining the uniform diameter through its height during the test; the plates are then not in contact with porous discs and so rubber bands exerts lateral pressure on the specimen. As many rubber bands as needed to maintain uniform diameter of cylindrical specimen and also to resist lateral pressures proportional to the applied vertical load during the test, shall be used. The inside surface of segment plates shall be lubricated to reduce friction between rubber membrane around soil specimen and the plates. The function of segmental stainless steel plates is to uniformly distribute the lateral load applied by rubber bands on the soil specimen.

Alternatively, the lubricated segment plates can be assembled around soil specimen by use of leather or nylon or polyester or polypropylene VELCRO straps of width generally between about ½" and 1" (12.7 mm and 25.4 mm). First, segment plates are fastened to VELCRO strap using 5-44 or M-3 screws as shown in FIG. 9 (other screw sizes may be used along with appropriate female threads in segment plates). Then the assembled plates are wrapped around the soil specimen and maintained in position by VELCRO strap as shown in FIG. 10. The rubber bands of thickness of generally about ⅛" (3.17 mm) are slipped on around the plates as shown in FIG. 11. The screws are unthreaded to remove the straps. The remaining rubber bands are then slipped on around the plates in the space earlier occupied by the VELCRO straps, as shown in FIG. 12(A). The flexible ring has now been installed around the soil specimen. The leather or nylon VELCRO straps can also be installed near the bottom of the plates, in addition to one shown at middle of the height in the figures, as considered necessary to properly install the rubber bands or rings.

FIG. 12B shows open reservoir made of acrylic or non-corrodible metal. When acrylic is used, the acrylic wall and the bottom shall be connected by weld-on plastic adhesive. In case of metal, normal weld shall be used. FIG. 12(C) shows that instead of weld, the acrylic or metal tube shall be screwed in the base plate when assembled 3-D device has been placed on base plate.

FIG. 12D shows a sealed chamber which can withstand lateral water pressure at least up to 150 psi (1034 kPa). For this chamber, first 3-D device shall be assembled on the metal base plate, then the side metal wall shall be installed and bolted to the base plate as shown in this figure. The water/fluid then can be filled, thereafter the top metal plate shall then be installed and bolted to the side wall. The O-ring or flat gasket shall seal the base plate and top plate to the cylindrical side walls. FIG. 12E shows another schematic detail of a sealed metal or acrylic chamber. For this detail a thick metal or acrylic cylindrical wall shall be used in which the holes can be drilled as shown in this figure. In cast acrylic cylindrical wall, the holes can also be casted to avoid drilling. The long bolts shall be inserted in the holes from the bottom and tightened from the top when top plate has been placed. Both bottom and top plates shall be made watertight by seating a flat gasket in between the plates and the side wall. In place of a flat gasket, either one 0-ring on the inner side of bolts or two O-rings on either side of the bolts can be provided; for seating O-rings, circular grooves both on the plates and side vertical wall has to be provided as considered necessary. For this detail, water/fluid shall be filled from the central hole in the top plate, through a polythene or nylon tube (diameter less than the diameter of the central hole) inserted in the central hole. The number of bolts and holes and their diameter shall be designed to resist the design lateral pressure in the chamber (generally 150 psi or 1034 kPa or greater). The bolts may be or may not be oiled or greased as considered necessary. The thickness of non-corrodible metal or acrylic side wall, which will have several holes, shall be designed to resist the maximum applied lateral pressure (generally 150 psi or 1034 kPa) in the chamber, critical section for design shall be located at the section containing the holes. The lateral pressure shall be applied in increments and after each increment, the bolts of FIG. 12 (D) or FIG. 12 (E) shall be tightened again to offset the elongation of bolts which may occur at each increment of lateral pressure in the chamber.

As an alternative to details shown for open reservoir and sealed metal or acrylic chambers in FIG. 12E, FIG. 12B, FIG. 12C, FIG. 12D and FIG. 12E, the open reservoir and sealed chambers as available in the industry can be used, but in most cases depending on the size of soil specimen, the available sizes of the open reservoirs may need to be redesigned and revised to fit 3-D device assembly.

In FIG. 12B and FIG. 12C, 3-D test device assembly has not been shown, although shown in FIG. 12C. In FIG. 12D and FIG. 12E. 3-Dimensional test device assembly, control panel and loading device for the water sealed metal or acrylic chamber has not been shown as these figures as these shall be the same as shown in FIG. 15 and FIG. 16. Control panel shall be connected to valves shown in these figures.

Sizes of segment plates, half brackets and rubber bands shown in FIG. 2 through FIG. 9 and described in the text above are based on soil specimen diameter of 2.87" (72.9 mm) in diameter. Diameter of soil specimen is also dependent on inside diameter of Shelby tubes or other type of samplers used for extracting the samples from a cohesive deposit. Inside diameter of Shelby tubes as per ASTM standards are 1.905" (48.42 mm), 2.87" (72.9 mm) and 4.76" (120.9 mm). The diameter of circular arch shaped segment plates and two half brackets shall depend on the diameter soil specimen. Number of segment plates shall be generally about 8, 10 and 16 for soil specimen of 1.905" (48.42 mm), 2.87" (72.9 mm) and 4.76" (120.9 mm), respectively. For other specimen sizes, special design detail shall be used.

Because stainless steel does not corrode or rust with time, stainless steel has been mentioned to be used for circular segment plates and half brackets in above paragraphs and in FIG. 5A, FIG. 5B and FIG. 6. Aluminum Alloys of certain grades and selected grades of several alloy metals also do not tend to corrode or rust, therefore as an alternative to stainless steel, aluminum alloys of certain grades and selected grades of several alloy metals shall also be selected for the circular segment plates and half-brackets. The thickness of circular segment plates has been mentioned to be generally between about ⅛" and ⅜" (3.6 mm and 9.53 mm), however as an alternative, thickness of the circular segment plates and half-brackets shall vary generally between about ¹⁄₁₆" and ⅜" (1.8 and 9.53 mm) or other sizes for widths and thicknesses of segmented plates and brackets shall also selected, if so considered appropriate and necessary for workability. The selection of type of the metals and thicknesses for circular segment plates and half-brackets shall be based on economics, workability and design life. Circular segmental plastic plates could also be selected in place of metal plates, based on workability and design life. Screw and bolt sizes other than those given in above paragraphs and in FIG. 5A, FIG. 6, FIG. 7, FIG. 9 and other figures shall and could also be selected if so considered appropriate and necessary; the selection of other sizes of screws and bolts shall be based on economics, workability and availability in the industry/market. To clamp two-half brackets together, either detail as shown in FIG. 5A or FIG. 5B or some other appropriate similar detail shall be used, depending upon workability observed during installation. It may be noted that all screws shall have appropriate threads, but in these figures, threads have been shown in few screws and not in all screws in FIG. 5A and FIG. 5B. Also the inner overlapping plate length where two half brackets are connected may be thicker than outer overlapping plate length to provide longer threads in the inner plate for properly fastening the two-half brackets.

In above paragraphs, and in FIG. 2, FIG. 4, FIG. 7, FIG. 8, FIG. 10, FIG. 11, and FIG. 14, rubber bands have been mentioned for the flexible ring. Elastomeric rubber bands and rings both can have either rectangular or square or circular cross-section or cross-section of the shape of even an ellipse. Elastomeric rubber rings or bands (consisting of different types of rubber or rubber composites) with circular or cross-section or other round shapes may prove to be easier to slip on the segment plates, therefore, as an alternative, elastomeric bands or rings with circular or round cross-section or other different cross-sections shall also be used to slip on the segment plates in place of rubber bands or rings with square or rectangular cross-section. The thickness/diameter, modulus of elasticity and the tensile strength of elastomeric rings/bands and their total number shall be selected based on the design lateral resistance to be exerted by the flexible ring on the cylindrical soil specimen during the test.

(d) Cross-Sectional Area at a Given Load

Rubber membrane is used to encase the specimen to provide reliable protection against leakage and also for separation between soil specimen and the reservoir/chamber fluid. The membrane is sealed to the specimen cap and base with rubber O-rings. The flexible ring encasing the soil specimen maintains uniform diameter through its height. Area of cross section, A, for a given applied load at an instant of time t, is approximately given by:

$$A = \frac{A_c}{(1-\varepsilon_v)} \quad (1)$$

Where:
$A_c$=Average cross-sectional area of the specimen after consolidation and before beginning the test.
$\varepsilon_v$=Axial strain for the given axial load at any instant time t=$\Delta H/H$
$\Delta H$=Change in height of specimen during loading
H=height of specimen after consolidation.
D=Diameter of specimen after consolidation.

Each increment of load is maintained for 24 hours and drainage is allowed during the test. Therefore, pore-water pressures which develop instantaneously after application of the load, are allowed to dissipate almost to a zero value. Thus at each increment of load, the settlements in the soil specimen continues to occur from beginning of the application of increment for all the 24 hours. Eq. 1 does not take into account the lateral settlement which occurs at each increment of load. For the three-dimensional consolidation test, the lateral displacement of the specimen during the test shall also be measured by two linear variable differential transformers (LVDTs) placed diametrically opposite to each other to measure radial displacement and the above equation shall be corrected when enough data is available. In the drawings, LVDTs and their mounting system has not been shown. Volume of specimen shall be calculated based on measured height, measured diameter and volume pore water expelled from the specimen. Area of specimen shall be calculated based on measured diameter or based on calculations.

(e) Lateral Resistance Provided by Rubber Bands, Membrane and Elastic Filter Fabric During the test, when an additional vertical load increment is applied, the lateral stress increases which thereby is resisted by the elastomeric rubber bands/rings, rubber membrane and filter fabric. These elastic elements stretch/expand during the test; the magnitude of expansion or increase in diameter is proportional to the lateral load and their modulus of elasticity. The increase in lateral stress for each increment of load shall be equal to vertical stress times Poisson's ratio. The magnitude of the lateral stress cannot be allowed to exceed the tensile strength of these elastic elements. The magnitude of lateral stress is proportional to vertical stress applied during the test. Therefore, vertical load to be applied during the test has to be limited so that the tensile strength of these elements is not exceeded. For this purpose, the vertical load shall not be increased any further, when the rate of increase in diameter as measured by LVDTs increases suddenly, indicating that the failure is approaching. If LVDTs are not used, and when vertical settlement continues to increase at the same load increment, the vertical load shall not be increased any further and it shall be assumed that tensile strength of elastomeric rubber bands or rings is about to occur.

A calibration device as shown in FIG. 13 and FIG. 14 shall be used to provide the data for the magnitude of lateral stress versus the increase in diameter (or lateral strain) of rubber membrane/elastomeric rubber bands/filter fabric. This data shall help in calculating the combined modulus of elasticity of these elastic elements installed around the specimen. To measure increase in diameter of these elastic elements during calibration, LVDTs shall be installed around the segment plates/rubber bands. In these drawings, the LVDTs and their mounting system has not been shown. Alternatively, the increase in diameter shall be calculated using the measured drop in water reservoir.

The transparent Perspex or clear acrylic cylindrical reservoir, 2" to 8" (50 to 200 mm) in diameter, shall be raised by a foot (0.3 m) or less, each time to expand the calibration device as shown in FIG. 13 and also when flexible ring is mounted on calibration device as shown in FIG. 14 to provide data of expansion of these elastic elements with increase in water head or hydraulic pressure. The reservoir can be raised to any height varying between 2 and 8 ft. (0.6 and 2.4 m) or to greater height depending on the headroom of the laboratory. If higher pressures are needed for calibration, the water reservoir shall be disconnected and a hydraulic pump of a very low capacity (maximum of 40 psi, i.e., 276 kN/m$^2$) shall be connected to the calibration device to perform the calibration up to 20 psi (138 kN/m$^2$) pressure. The pressure shall be increased in increments of 0.5 to 1 psi (3.5 to 6.9 kN/m$^2$) or less. Alternatively, if higher pressures are needed for calibration, the water reservoir shall be capped by a water/air tight cap and the reservoir connected to a pressure chamber which is pressurized by a nitrogen cylinder or air compressor and pressures up to 20 psi (138 kN/m$^2$) shall be applied to perform calibration. The pressure shall be applied in increments of 0.5 to 1 psi (3.5 to 6.9 kN/m$^2$) or less.

The calibration device consists of a porous stainless steel or non-corrodible metal tube with end caps sealed for water tightness. The rubber membrane of thickness between 1 and 5 mm is mounted on porous stainless steel tube. The rubber membrane is clamped at the ends of porous stainless steel tube for water tightness. On one end, a brass tube shall outlet the porous stainless steel tube to remove the air bubbles from water when hydraulic fluid is filled in the porous steel tube. When air bubbles are not seen coming out from the tube, the valve shall be closed. The brass tube on the other end of the porous stainless tube shall lead towards the reservoir. The thinner rubber membranes can be mounted on each other to make up the required overall thickness of membrane (say between 1 and 5 mm).

The calibration of the calibration device as shown in FIG. 13 shall be first done and data recorded in Table 1. Thereafter, first filter fabric, then rubber membrane, (same as to be used during the test around the soil specimen), then segment plates and finally rubber bands shall be mounted on the calibration device. The segment plates shall be mounted with the help of half-brackets or VELCRO straps as previously detailed in FIG. 5B through FIG. 11. The calibration of the calibration device shall be done raising reservoir by half a foot (0.15 m) or a foot (0.3 m) or by pump pressure or chamber pressure each time by 0.5 psi (3.5 kN/m$^2$) or less. The calibration data shall be recorded in Table 2. The lateral stress exerted by rubber membrane of thickness between 1 and 5 mil (mm) of calibration device shall be deducted from the lateral stress exerted by the calibration device (i. e., rubber membrane of calibration device) plus the flexible ring [i.e. consisting of rubber membrane (of thickness between 0.5 mm and 5 mm) wrapped around the soil specimen, filter fabric and rubber bands], for determining the value of lateral stress being exerted by the flexible ring on the soil specimen at various levels of lateral strain, when vertical load is applied during the test. The calibration data shall also be used to calculate the combined modulus of elasticity of these elastic elements. For test method shown in FIG. 2, calibration shall be done on flexible ring consisting of the rubber membrane, segment plates and rubber bands. Lateral strain shall be calculated from the value of radial displacement measured by two LVDTs, placed diametrically opposite to each other. The value of radial displacement can also be calculated using the measured drop of level in the water reservoir. The product of lateral strain with combined modulus of elasticity shall provide the value of lateral stress at any instant of time during application of vertical load during the test.

There is a limit for the vertical load which can be applied during the test, as explained above, this limit shall depend on the tensile strength of the elastomeric rubber bands. For higher vertical load, the elastomeric rubber bands shall be replaced by a jacket consisting of stainless steel or non-corrodible metal springs, which can stretch and also resist vertical loads up to 32 tsf (3.06 MPa). In this case, calibration shall be done for the spring jacket in place of elastomeric rubber bands.

Even triaxial compression tests do not provide accurate estimate of horizontal and vertical settlements and modulus of elasticity because lateral stresses do not increase but remain equal to applied chamber pressure throughout the test, i.e. the lateral stresses do not increase as is estimated by theory of elasticity.

(f) Loading Device for Vertical Load

Incremental consolidation load frame/test system shall be the same as described in ASTM D-2435 and AASHTO T-216. The test shall be performed at vertical load increments of ½, 1, 2, 4, 8, 16 and 32 tsf (Note: 1 tsf=0.09576 MPa). Each load increment shall be maintained for 24 hours and readings taken at intervals described in ASTM D-2435. The test device as shown in FIGS. 2, 3 and 4 are adaptable to these loading devices.

As shown in FIG. 12A, the open reservoir containing 3-D consolidation device shall be used with conventional incremental loading device in accordance with ASTM D-2435 for performing tests. Alternatively, a chamber system similar to the one used for triaxial compression tests, shall be used for performing 3-D consolidation tests as shown in FIG. 15. The chamber for applying lateral pressure on 3-D consolidation specimen, axial loading system and control panel, in general shall be in accordance with ASTM Designation D4767-11. Because the height of specimen for 3-D consolidation tests shall be selected between 1" (25.4 mm) and half to three-quarter of the diameter of the soil specimen, the height of chamber to be used for 3-D consolidation test shall be about half or less than half of the height of the triaxial chamber. It may be noted that the height of the soil specimen for triaxial compression tests is greater than diameter of specimen and is about 2 times the diameter. Using triaxial axial loading system, either (a) the load shall be applied in the same increments as described in the above paragraph and held constant for 24 hours or (b) the strain controlled load test can also be performed, applying load to produce a selected vertical displacement at the beginning of each increment and then load held constant for 24 hours and measuring the consolidation settlement. The chamber system to apply lateral pressure on 3-D consolidation sample can also be used with incremental load frame/test system as shown in FIG. 16. The size of incremental loading system as shown in FIG. 16, is greater than the size of the incremental loading system required for open reservoir system shown in FIG. 12(A), due to chamber clamping rods. Therefore, the incremental loading system to be used with the chamber system, shall be larger in width and also height and shall be designed to accommodate the larger lateral dimension and height of chamber.

When the 3-D consolidation test is required to be performed in-situ condition (such as in partially saturated condition), system for applying vacuum and performing the back pressure saturation included in the control panel as shown in FIG. 15 and FIG. 16 shall be omitted. In many cases in the field, 100% saturation of partially saturated soils may never or may rarely occur in the life time of a structure, therefore, 3-D consolidation tests in in-situ moisture conditions may also be important. When, in-situ horizontal stresses are applied in the chamber system, at higher vertical load increments, the air in partially saturated soils either may get expelled out or may get dissolved and 100% saturation may be achieved at higher load increments, and therefore the same test may also provide 3-D consolidation properties, initially in partially saturated conditions and then at higher load increments in 100% saturated conditions. However, if the test is to be performed in 100% saturated conditions, then vacuum and back saturation as shown in control panel shall be used.

There are some important advantages of using a chamber system along with incremental consolidation load frame and triaxial axial loading system. In the chamber filled with water, fluid pressure can be applied equivalent to insitu horizontal earth pressure calculated for the depth from where the soil specimen was extracted for performing the consolidation test. Incremental consolidation load frame or triaxial axial loading system then shall predict both vertical and horizontal settlements of the soil at various values of loads at that particular depth. If there is thick soil deposit, and soil specimen have been extracted from various depths, a detailed data of horizontal and vertical settlements at various load increments shall be available at various depths of the same soil deposit. This will also help in providing data of insitu modulus of elasticity of soil at various depths.

In general, the horizontal stresses computed from the theory of elasticity are function of Poisson's ratio. However, vertical stresses resulting from normal stresses applied to the surface are always independent of Poisson's ratio. Vertical and horizontal stresses caused by strip load are also independent of Poisson' ratio (Lambe and Whitman, 1969). Horizontal stresses caused under a circular area depend on Poisson's ratio. Therefore, in three-dimensional consolidation tests, it is important that horizontal stresses caused by vertical stress on top of the specimen be approximately equal to those predicted by theory of elasticity either for strip load or for circular load. In three dimensional consolidation test, as vertical load is increased, the horizontal resistance on the sample increases as a product of lateral strain in rubber bands/membrane/filter fabric and its modulus of elasticity. Lateral strain during the test is calculated from measurements by LVDT. Combined modulus of elasticity of rubber bands, rubber membrane and elastic filter fabric is measured by the calibration device at various values of lateral strain. Therefore, ideally or theoretically, the combined modulus of elasticity of rubber bands, rubber membrane and elastic filter fabric during 3-D consolidation test should develop an increase in lateral resistance which should be equal to the increase estimated to occur in soil by the theory of elasticity at the same increment of the vertical load The various types of elastomeric rubber bands or rings are manufactured and the modulus of elasticity of these types can very between 100 to 800 psi (689 to 5516 kPa). The lateral resistance shall also depend on the thickness, width (or diameter if circular cross-section) and number of elastomeric rubber bands. Therefore, for three-dimensional consolidation tests, it shall be advisable to select the sizes and number of elastomeric rubber bands and their modulus of elasticity with the consideration that the increase in lateral resistance during the 3-D consolidation test is approximately the same as the increases in horizontal stresses in soil predicted by theory of elasticity.

(g) Mounting Device for LVDT and Strain Gages

LVDT can measure increase in circumference when wrapped around the specimen using a flexible attachment. LVDT can also measure radial displacement or radial expansion when suitably mounted radially on diametrically opposite sides. A frictionless U-frame device is shown in FIG. 17 to mount LVDT. The LVDT is attached to a U-shape device which rests on frictionless bearings. The vertical side of the U-shape device is in contact with 3-D device, and when soil specimen radially expands, the U-shaped device moves out radially displacing the LVDT to provide the measurement of radial displacement/expansion. In place of LVDT, a specially designed strain gage mounted on a thin stainless steel or a selected type of con-corrodible metal sister bar can also be attached to this U-Shaped device, to measure radial strain. The radial displacement then can be calculated as strain times length of the metal sister bar. Vertical face of the U-Frame in contact with 3-D device shall be lubricated with oil/grease to reduce friction between them. Either two LVDTs or strain gages on diametrically opposite sides of the specimen or 4 LVDTs or strain gages 90 degrees apart shall be used to monitor radial expansion of specimen during the test. The frictionless U-frame is placed between the 3-D device and the chamber or open reservoir wall and is properly supported on bottom platen of chamber or of open reservoir If LVDT is directly placed in contact with 3-D device to measure radial expansion, then it is very likely that LVDT probe in touch with specimen shall bend and become inclined instead of remaining horizontal when the soil specimen radial expands but also vertically settles. U-shaped device resting on frictionless bearings can also be used to measure lateral displacement of soil specimen during triaxial test on soils or of clay or rock specimen during uniaxial compressive tests.

In FIG. 17, detail shown for LVDT is conceptual, its shape will vary from manufacturer to manufacturer. LVDT or strain gages shall be required to be water proof. However, for open reservoir system as shown in FIG. 12A, the rear body of the LVDT can be taken out of a port through reservoir wall, then cables/wires will protrude out of the LVDT body outside of the reservoir in atmosphere. The port shall be property sealed so that water does not leak out from the reservoir. The LVDT probe when sliding in to its housing will need to be watertight.

From above, it is clear that the design of open reservoir, sealed metal chamber, triaxial type chamber and loading system, and incremental loading device system as presently available in the industry, may need to be re-designed to adapt or fit to the three-dimensional consolidation device (3-D device), depending upon the size of soil specimen.

(h) Conclusions

Three-dimensional consolidation device consists of a flexible ring. Flexible ring consists of filter fabric around the soil specimen, rubber membrane around the filter fabric, circular segmental plates around the membrane and elastomeric rubber bands or rings or spring loaded jacket around the segmental plates to allow both horizontal and vertical displacements, dissipation of excess pore-water pressures in both horizontal and vertical directions, and increased lateral resistance with each increment of vertical load, as occurs in subsurface soils when vertical load is incrementally applied. In open reservoirs, the lateral pressures cannot be applied, so test is to be performed in the conventional way. In sealed chambers and triaxial type chambers, the lateral pressure approximately equal to theoretically calculated at the depth from where the soil sample was extracted, can be applied can be applied to perform the test simulating the insitu condition and environment in the geotechnical laboratories. The mounting device resting on frictionless bearings, placed between specimen and chamber or reservoir wall and properly supported on the base plate of the chamber or open reservoir, shall allow horizontal displacement to be measured by LVDT or strain gages, without allowing bending of the LVDT probe or strain gage. The lateral or radial expansion of the soil specimen during the test shall be measured by the LVDT or strain gage. If LVDT or strain gage is not used, the lateral or radial expansion of the soil specimen shall be calculated using the measured vertical settlement of the specimen and the measured amount of pore-water expelled out from the specimen to the burette during the test.

The calibration device consisting of porous metal tube wrapped around the rubber membrane and the flexible ring and a vertical movable reservoir to apply water pressure, shall be used to determine the modulus of elasticity of the elastic elements (rubber membrane, rubber bands/rings and filter fabric), for calculating the lateral resistance provided by elastic elements, based on modulus of elasticity of the elastic elements and measured radial expansion. For higher pressures for calibration, the sealed reservoir shall be connected to a pressure chamber with a control valve.

With the invention of test device for determining three-dimensional consolidation properties of soils using a flexible ring in place of a rigid ring of the one-dimensional consolidation test, as detailed above, it shall be possible to determine the following for both for normally and overconsolidated soils: (i) Horizontal and vertical settlements, (ii) Coefficient of consolidation in vertical direction ($c_v$) when both horizontal and vertical settlements are taking place like those which occur insitu at various depths when vertical loads are applied at the surface, (iii) Coefficient of consolidation in horizontal direction ($c_{hi}$) when both horizontal and vertical settlements are taking place like those which occur insitu at various depths when vertical loads are applied at the surface, (iv) three-dimensional coefficient of consolidation, $c_{3-D}$, (i.e. resultant of $c_v$ and $c_{hi}$), when both horizontal and vertical settlements are taking place like those which occur insitu at various depths when vertical loads are applied at the surface, (v) Correlations between $c_v$ with depth and with vertical and horizontal stresses, (vi) Correlations between $c_{hi}$ with depth and with vertical and horizontal stresses, (vii) Correlations between ratio $c_{hi}/c_v$ with depth and also with increase in vertical and horizontal stresses, (viii) Modulus of elasticity (E) at various depths and vertical loads, (ix) Correlations between E with depth and with vertical and horizontal stresses, (xii) Correlations of $c_v$, $c_{hi}$, and E with density of soils, and (xiii) Although laboratory soil tests such as one-dimensional consolidation test and triaxial compression tests are being conducted for last more than 100 years, these values as described above have not been determined accurately in laboratory, but with the invention of test device for determining three-dimensional consolidation properties allowing both vertical and horizontal settlements and dissipation of excess pore-water pressures, it will be possible to determine these values correctly because now field conditions shall be simulated in the geotechnical testing laboratories.

TABLE 1

Form for entering data to calibrate the calibration device

| Serial No. | Water Head in ft. or m or Water Pressure in psi or kPa above Centerline of Porous Stainless steel Tube | Increase in Diameter of membrane, Δd (inch or mm) as measured by LVDT or calculated from head measured in reservoir | Lateral Strain, $\varepsilon_l$ = Δd/d | Water Pressure ($p_w$) in psi (kg/mm$^2$) | Modulus of Elasticity (E) of rubber n psi or kg/mm$^2$ |
|---|---|---|---|---|---|
| | | | | | |
| | | .......... | ....... | .......... | ....... |
| | | | | | |
| | | | | | |
| | | | | | |
| | | | | | |
| | | | | | |
| | | | | | |
| | | | | | |
| | | | | | |

Outside diameter of porous stainless tube with rubber membrane, d = ......,

Length of rubber membrane between end clamps, L = ........

Cross-sectional Area of device, A = π d$^2$/4, Volume of device = A*L

Inside diameter of reservoir = $d_r$, Cross-sectional Area of reservoir, $A_r$ = π $d_r^2$/4

Increase in Diameter of device, Δd, as measured by LVDWT

E of rubber membrane = $p_w/\varepsilon_l$

TABLE 2

Form for entering data to calibrate the flexible ring

| Serial No. | Water Head in ft. or m or Water pressure in psi or kPa above the Centerline of Porous Stainless Steel Tube | Increase in Diameter of rubber bands, Δd (inch or mm) | Lateral Strain, $\varepsilon_{rb} =$ $\Delta d/d_p$ | Water Pressure ($p_w$) in psi or kPa | Combined Modulus of Elasticity (E) of rubber bands, filter fabric & rubber membrane in psi or kPa |
|---|---|---|---|---|---|
| | | | | | |
| | | ......... | ....... | ......... | ....... |
| | | | | | |
| | | | | | |
| | | | | | |
| | | | | | |
| | | | | | |
| | | | | | |
| | | | | | |
| | | | | | |

Outside diameter of rubber bands before beginning calibration, d = ......,
Length of rubber membrane between end clamps, L = ........
Increase in Diameter of rubber bands, Δd = .........
Outside diameter of segmental plates before beginning of test = $d_p$
Outside diameter of filter fabric = $d_f$
Outside diameter of rubber membrane = $d_m$
Lateral strain of rubber bands, $\varepsilon_{rb} = \Delta d/d$

REFERENCES

ASTM Standards (2011), Standard Test Method for Determining One-Dimensional Consolidation Properties of Soils, ASTM D2435/D2435 M-11, *American Society of Materials*, Philadelphia, Pa.

ASTM Standards (2011) Standard Test Method for Consolidated Undrained Triaxial Compression Test for Cohesive Soils. ASTM: D4767-11.

AASHTO (2012), Standard Method of Test for One-Dimensional Consolidation Properties of Soils, *American Association of State Highway and Transportation Officials*, Washington, D.C.

Fang, H (1990), Foundation Engineering Handbook, 2$^{nd}$ Edition, Van Nostrand Reinhold, New York.

HRB (1973), Estimating Consolidation Settlements of Shallow Foundations on Overconsolidated Clay, Application Bulletin prepared by Committee A2L02, *Properties of Soil and Rock, Highway Research Board*, Washington, D.C.

Perloff, W. H., and Baron, W. (1976), SOIL MECHANICS, John Wiley and Sons, New York.

Skempton, A. W., and Bjerrum, L. (1957), A Contribution to the Settlement Analyses of Foundations on Clay, *Geotechnique* 7, No. 3

Terzaghy, K, Peck, B. P., Mesri, G. (1996), Soil Mechanics in Engineering Practice, Wiley-Interscience, New York Winterkorn H. F., and Fang, H. (1975), Foundation Engineering Handbook, Van Nostrand Reinhold Company, New York.

The invention claimed is:

1. The test system to determine three-dimensional consolidation properties of soils, the test system comprising:
  a. A test device comprising;
    (i) a triaxial type loading system or incremental loading system;
    (ii) a triaxial type control panel;
    (iii) a chamber comprising metal or acrylic vertical walls, a top plate, and a base plate; wherein the metal or acrylic vertical walls are held in place by the top plate and the base plate by two or more bolts or clamping rods between the top plate and the base plate;
    (iv) a first porous disc, said porous disc resting on the base plate to receive a soil specimen within a chamber or an open reservoir;
    (v) a second porous disc, placed on top of the soil specimen;
    (vi) a loading head placed on top of the second porous disc;
    (vii) a filter fabric placed such that the filter fabric surrounds and is in contact with the soil specimen;
    (viii) a rubber membrane placed such that the rubber membrane surrounds and is in contact with the filter fabric;
    (ix) a plurality of segmented circular shaped metal plates assembled vertically such that the assembled segmented plates surround and are in contact with the rubber membrane, and wherein each of the segmented metal plates contains at least one screw mount for the removable attachment of two horizontal separate half-circular brackets, a horizontal nylon hook and loop strap, or a horizontal leather hook and loop strap for vertical and horizontal positioning of each of the segmented metal plates; wherein the screw mounts are located at the mid-height or other predetermined heights of each of the segmented metal plates; wherein each of the segmented metal plates extend vertically beyond the first and second porous disc;

(x) at least one elastomeric rubber band or ring placed such that each of the at least one elastomeric rubber bands or rings surround and are in contact with each of the segmented metal plates;

b. and a calibration device for determining a combined modulus of elasticity of the filter fabric, the rubber membrane, segmented metal plates and the at least one elastomeric rubber band or ring, the calibration device comprising:

(xi) a water reservoir, wherein the water reservoir has a vertical position defined by a vertically movable metal bracket;

(xii) a horizontal porous metal tube connected to the vertically movable water reservoir via at least one tube, wherein the porous metal tube is configured to be surrounded and sealed by an additional rubber membrane and wherein the additional rubber membrane is configured to be surrounded by a combination of the filter fabric, the rubber membrane, the segmented metal plates, and the at least one elastomeric rubber band or ring.

2. The test system to determine three-dimensional consolidation properties of soils, the test system comprising:

a. A test device comprising;

(i) a triaxial type loading system or incremental loading system;

(ii) an open metal or acrylic reservoir comprising a metal or acrylic cylindrical vertical wall and circular base plate, wherein metal wall and base plate held in place by bolts, and acrylic wall and base plate held in place by threads in the wall and the base plate;

(iii) a first porous disc, said porous disc resting on the base plate to receive a soil specimen within a chamber or an open reservoir;

(iv) a second porous disc, placed on top of the soil specimen;

(v) a loading head placed on top of the second porous disc;

(vi) a filter fabric placed such that the filter fabric surrounds and is in contact with the soil specimen;

(vii) a rubber membrane placed such that the rubber membrane surrounds and is in contact with the filter fabric;

(viii) a plurality of segmented circular shaped metal plates assembled vertically such that the assembled segmented plates surround and are in contact with the rubber membrane, and wherein each of the segmented metal plates contains at least one screw mount for the removable attachment of two horizontal separate half-circular brackets, a horizontal nylon hook and loop strap, or a horizontal leather hook and loop strap for vertical and horizontal positioning of each of the segmented metal plates; wherein the screw mounts are located at the mid-height or other predetermined heights of each of the segmented metal plates; wherein each of the segmented metal plates extend vertically beyond the first and second porous disc;

(ix) at least one elastomeric rubber band or ring placed such that each of the at least one elastomeric rubber bands or rings surround and are in contact with each of the segmented metal plates;

b. and a calibration device for determining a combined modulus of elasticity of the filter fabric, the rubber membrane, segmented metal plates and the at least one elastomeric rubber band or ring, the calibration device comprising:

(x) a water reservoir, wherein the water reservoir has a vertical position defined by a vertically movable metal bracket;

(xi) a horizontal porous metal tube connected to the vertically movable water reservoir via at least one tube, wherein the porous metal tube is configured to be surrounded and sealed by an additional rubber membrane and wherein the additional rubber membrane is configured to be surrounded by a combination of the filter fabric, the rubber membrane, the segmented metal plates, and the at least one elastomeric rubber band or ring.

3. The test system to determine three-dimensional consolidation properties of soils according to claim 1, wherein the test device further comprises:

(xiii) at least one LVDT or strain gage removably attached to a U-frame; wherein the U-frame in contact with the at least one of the elastomeric rubber band or ring; wherein the U-frame rests on ball bearings such that during radial expansion of the soil specimen, the U-frame prevents the LVDT or strain gage from being inclined due to the vertical settlement of the soil specimen.

4. The test system to determine three-dimensional consolidation properties of soils according to claim 2, wherein the test device further comprises:

(xii) at least one LVDT or strain gage removably attached to a U-frame; wherein the U-frame in contact with the at least one of the elastomeric rubber band or ring; wherein the U-frame rests on ball bearings such that during radial expansion of the soil specimen, the U-frame prevents the LVDT or strain gage from being inclined due to the vertical settlement of the soil specimen.

* * * * *